US006678562B1

(12) United States Patent
Tepper et al.

(10) Patent No.: US 6,678,562 B1
(45) Date of Patent: Jan. 13, 2004

(54) COMBINED TISSUE/BONE GROWTH STIMULATOR AND EXTERNAL FIXATION DEVICE

(75) Inventors: John C. Tepper, Carrollton, TX (US); Richard M. Bryant, Clemmons, NC (US)

(73) Assignee: AMEI Technologies Inc., Wilmington, DE (US)

( * ) Notice: Subject to any disclaimer, the term of this patent is extended or adjusted under 35 U.S.C. 154(b) by 0 days.

(21) Appl. No.: 09/526,136

(22) Filed: Mar. 14, 2000

Related U.S. Application Data

(60) Provisional application No. 60/175,678, filed on Jan. 12, 2000.

(51) Int. Cl.[7] .............................. A61N 1/08; A61N 1/10; A61N 1/18; A61N 1/20; A61N 1/32
(52) U.S. Cl. ........................................... 607/51; 606/54
(58) Field of Search ................... 606/54–75; 607/50–52

(56) References Cited

U.S. PATENT DOCUMENTS

| | | | |
|---|---|---|---|
| 3,604,414 A | 9/1971 | Borges ..................... 128/92 D |
| 3,783,880 A | * 1/1974 | Kraus | |
| 3,918,440 A | * 11/1975 | Kraus | |
| 4,102,339 A | 7/1978 | Weber et al. ............. 128/92 E |
| 4,312,336 A | 1/1982 | Danieletto et al. ........ 128/92 A |
| 4,488,542 A | 12/1984 | Helland .................... 128/92 A |
| RE31,809 E | 1/1985 | Danieletto et al. ........ 128/92 A |
| 4,549,547 A | 10/1985 | Brighton et al. .......... 128/419 F |
| 4,604,997 A | 8/1986 | DeBastiani et al. ....... 128/92 A |
| 4,620,543 A | * 11/1986 | Heppenstall et al. | |
| 4,621,627 A | 11/1986 | DeBastiani et al. ..... 128/92 ZZ |
| 4,628,919 A | 12/1986 | Clyburn ................. 128/92 ZK |
| 4,793,325 A | * 12/1988 | Cadossi et al. | |
| 4,828,277 A | 5/1989 | DeBastiani et al. ....... 279/1 SG |
| 4,889,111 A | * 12/1989 | Ben-Dov | |
| 4,946,179 A | 8/1990 | DeBastiani et al. ....... 279/1 SG |
| 4,957,496 A | 9/1990 | Schmidt ..................... 606/70 |
| 4,978,347 A | 12/1990 | Ilizaarov ..................... 606/54 |
| 4,988,349 A | 1/1991 | Pennig ....................... 606/58 |
| 5,019,077 A | 5/1991 | DeBastiani et al. ........... 606/54 |
| 5,026,374 A | 6/1991 | Dezza et al. .................. 606/72 |
| 5,056,518 A | 10/1991 | Pethica et al. ............ 128/419 F |
| 5,062,844 A | * 11/1991 | Jamison et al. | |
| 5,067,954 A | 11/1991 | Ilizarov ....................... 606/58 |
| 5,129,903 A | 7/1992 | Luhr et al. ................... 606/71 |

(List continued on next page.)

FOREIGN PATENT DOCUMENTS

SU          1271528       * 11/1986

OTHER PUBLICATIONS

PCT Search Report PCT/US00/35527, May 4, 2001.
"Orthopedic Fixation Devices," Richard M. Slone, M..D., et al., RadioGraphics, vol. II, #5, pp. 823–847, 1991.
"Medical Compartment Osteoarthritis" Brochure, Orthofix, Jan. 1998.

*Primary Examiner*—Mark Bockelman
(74) *Attorney, Agent, or Firm*—Baker Botts L.L.P.

(57) ABSTRACT

A combined tissue/bone growth stimulator and external fixation device is provided to aid in the treatment of fractures, osteotomies, soft tissue injuries, and reconstructive surgery and to reduce the likelihood of complications. The tissue/bone growth stimulator apparatus includes an external fixation device for stabilization of a selected portion of a patient. The tissue/bone growth stimulator apparatus also includes an electrical circuit attached to and forming an integral component of the external fixation device and operable to generate an electrical drive signal. The tissue/bone growth stimulator apparatus also includes a cable adapted to connect the electrical drive signal to a stimulator portion operable to provide an electromagnetic field to stimulate the growth of bone and tissue at the selected portion of the patient and/or at other portions of the patient. More particularly, the electromagnetic field may be produced by directing a current through the external fixation device into the patient.

27 Claims, 10 Drawing Sheets

U.S. PATENT DOCUMENTS

| | | | |
|---|---|---|---|
| 5,209,750 A | 5/1993 | Stef | 606/54 |
| 5,281,224 A | 1/1994 | Faccioli et al. | 606/62 |
| 5,292,322 A | 3/1994 | Faccioli et al. | 606/59 |
| 5,304,180 A | 4/1994 | Slocum | 606/69 |
| 5,314,401 A | 5/1994 | Tepper | 600/14 |
| 5,320,622 A | 6/1994 | Faccioli et al. | 606/58 |
| 5,320,623 A | 6/1994 | Pennig | 606/59 |
| 5,330,477 A | 7/1994 | Crook | 606/69 |
| 5,342,360 A | 8/1994 | Faccioli et al. | 606/56 |
| 5,358,504 A | 10/1994 | Paley et al. | 606/56 |
| 5,376,090 A | 12/1994 | Pennig | 606/54 |
| 5,413,596 A * | 5/1995 | Kronberg | |
| RE34,985 E | 6/1995 | Pennig | 606/58 |
| 5,433,720 A | 7/1995 | Faccioli et al. | 606/87 |
| D361,555 S | 8/1995 | Erickson et al. | D14/114 |
| 5,437,667 A | 8/1995 | Papierski et al. | 606/55 |
| 5,441,527 A | 8/1995 | Erickson et al. | 607/51 |
| 5,443,464 A | 8/1995 | Russell et al. | 606/54 |
| 5,458,558 A * | 10/1995 | Liboff et al. | |
| 5,458,627 A | 10/1995 | Baranowski, Jr. et al. | 607/51 |
| RE35,129 E | 12/1995 | Pethica et al. | 607/2 |
| D367,529 S | 2/1996 | Price et al. | D24/127 |
| D367,531 S | 2/1996 | Price et al. | D24/143 |
| 5,496,319 A | 3/1996 | Allard et al. | 606/56 |
| 5,524,624 A | 6/1996 | Tepper et al. | 128/660.03 |
| 5,545,162 A | 8/1996 | Huebner | 606/57 |
| D373,632 S | 9/1996 | Price et al. | D24/127 |
| D373,635 S | 9/1996 | Price et al. | D24/140 |
| 5,558,654 A | 9/1996 | Hardy | 604/322 |
| 5,565,005 A | 10/1996 | Erickson et al. | 607/51 |
| 5,591,164 A | 1/1997 | Nazre et al. | 606/59 |
| 5,601,551 A | 2/1997 | Taylor et al. | 606/54 |
| 5,620,449 A | 4/1997 | Faccioli et al. | 606/98 |
| 5,653,707 A | 8/1997 | Taylor et al. | 606/54 |
| 5,662,648 A | 9/1997 | Faccioli et al. | 606/54 |
| 5,662,650 A | 9/1997 | Bailey et al. | 606/59 |
| 5,681,313 A | 10/1997 | Diez | 606/69 |
| 5,681,318 A | 10/1997 | Pennig et al. | 606/98 |
| 5,688,271 A | 11/1997 | Faccioli et al. | 606/54 |
| 5,702,389 A | 12/1997 | Taylor et al. | 606/54 |
| 5,707,370 A | 1/1998 | Berki et al. | 606/59 |
| 5,728,095 A | 3/1998 | Taylor et al. | 606/54 |
| 5,728,096 A | 3/1998 | Faccioli et al. | 606/54 |
| 5,743,898 A | 4/1998 | Bailey et al. | 606/54 |
| 5,766,179 A | 6/1998 | Faccioli et al. | 606/98 |
| 5,766,231 A | 6/1998 | Erickson et al. | 607/51 |
| 5,797,908 A | 8/1998 | Meyers et al. | 606/54 |
| 5,803,924 A | 9/1998 | Oni et al. | 606/54 |
| 5,827,282 A | 10/1998 | Pennig | 606/54 |
| 5,827,283 A | 10/1998 | Groiso et al. | 606/57 |
| 5,827,286 A | 10/1998 | Incavo et al. | 606/71 |
| 5,855,580 A | 1/1999 | Kreidler et al. | 606/71 |
| 5,863,292 A | 1/1999 | Tosic | 606/56 |
| 5,891,143 A | 4/1999 | Taylor et al. | 606/56 |
| 5,893,850 A | 4/1999 | Cachia | 606/72 |
| 5,897,555 A | 4/1999 | Clyburn et al. | 606/54 |
| 5,902,302 A | 5/1999 | Berki et al. | 606/59 |
| 5,902,304 A | 5/1999 | Walker et al. | 606/71 |
| 5,928,234 A | 7/1999 | Manspeizer | 606/61 |
| 5,941,879 A | 8/1999 | Walulik et al. | 606/61 |
| 5,964,763 A | 10/1999 | Incavo et al. | 606/71 |
| 5,997,490 A * | 12/1999 | McLeod et al. | |
| 6,187,005 B1 | 2/2001 | Brace et al. | 606/61 |
| 6,203,548 B1 | 3/2001 | Helland | 606/105 |
| 6,235,029 B1 | 5/2001 | Faccioli et al. | 606/54 |
| 6,328,737 B1 | 12/2001 | Moorcroft et al. | 606/57 |

\* cited by examiner

COMBINED TISSUE/BONE GROWTH STIMULATOR AND EXTERNAL FIXATION DEVICE

RELATED PATENT APPLICATIONS

This application claims the benefit of U.S. Provisional Application Ser. No. 60/175,678 entitled "Combined Tissue/Bone Growth Stimulator and External Fixation Device" filed Jan. 12, 2000.

TECHNICAL FIELD OF THE INVENTION

The present invention relates in general to medical devices and more particularly to a combined tissue/bone growth stimulator and external fixation device.

BACKGROUND OF THE INVENTION

External fixation devices are often used in the treatment of fractures, soft tissue injuries and reconstructive surgery. External stabilization devices or splints are frequently used to position a fracture or osteotomy in proper alignment during the healing process. External fixation devices may also be used in a variety of clinical procedures to lengthen or shorten bone, or to delay joint replacement. Multiple bone screws are often used to provide interfragmental compression or to attach plates which provide compression, prevent displacement of bone or tissue fragments and support the fractured bone or tissue fragments during healing. These screws, wires and/or pins are placed through one or both cortices of bone to properly position and align the fracture, non-union or osteotomy. Delayed union or non-union bone fractures are typically considered injuries that have not made satisfactory progress towards healing. External fixation devices allow easy access to wounds, adjustment during the course of healing and often allow more functional use of the fractured limb. Such devices may be used in place of a conventional cast.

For example, some conventional fixation devices may be used to adjustably secure a first bone portion above an osteotomy in a position relative to a second bone portion below the osteotomy. Unfortunately, many of these devices may impair a physician's ability to monitor the healing process and/or access the area surrounding the osteotomy. For example, some conventional fixation devices may block or limit examination techniques such as radiographic, ultrasonic and/or visual examination of a treatment site.

Pulsed electromagnetic field (PEMF) therapy has been used to treat therapeutically resistant problems of the musculoskeletal system. Examples of PEMF therapy include treatment of non-union bone fractures and delayed union bone fractures. PEMF therapy has also been used for treatment of various types of soft body tissue injuries.

PEMF therapy has been satisfactorily used in treating spinal fusion, failed arthrodeses, osteonecrosis, and chronic refractory tendinitis, decubitus ulcers and ligament, tendon injuries, osteoporosis, and Charcot foot. During PEMF therapy, an electromagnetic transducer coil is generally placed in the vicinity of the musculoskeletal injury or body tissue injury (sometimes referred to as the "target area" or "selected portion") such that pulsing the transducer coil will produce an applied or driving field that penetrates to the underlying damaged bone or other body tissue. PEMF therapy typically uses low-energy, timevarying electromagnetic fields.

However, the healing process may still require an extended time, even with the use of external fixation devices. Complications may sometimes occur from the use of external fixation devices in such procedures. Complications such as infection at the pin or screw interface with a patient, may result in pin loosening and lessen the effectiveness of the external fixation device.

SUMMARY OF THE INVENTION

In accordance with teachings of the present invention, disadvantages and problems associated with the use of external fixation devices have been substantially reduced or eliminated.

One aspect of the present invention is a combined tissue/bone growth stimulator and external fixation device to aid in the treatment of fractures, osteotomies, soft tissue injuries, and reconstructive surgery and to reduce the likelihood of complications. The tissue/bone growth stimulator apparatus includes an external fixation device for stabilization of a selected portion of a patient. The tissue/bone growth stimulator apparatus also includes an electrical circuit attached to and forming an integral component of the external fixation device and operable to generate an electrical drive signal. The tissue/bone growth stimulator apparatus also includes a cable adapted to connect the electrical drive signal to a stimulator portion operable to provide an electromagnetic field to stimulate the growth of bone and tissue at the selected portion of the patient and/or at other portions of the patent. More particularly, the electromagnetic field may be produced by directing a current through the external fixation device into the patient.

The external fixation device can interface with the patient using stabilization devices such as pins, bone screws, or wires which are implanted in the patient according to known methods. The external fixation device can act to stabilize, compress, or distend the selected portion of the patient. For example, the external fixation device can compress a bone fracture, aiding the treatment by increasing the contact area of the fracture and decreasing the fracture gap. The external fixation device may be selectively adjusted in length or position to aid in effective treatment. In one embodiment the length of the external fixation device can be selectively lengthened or compressed. For example, the frame fixation device may be gradually shortened to compress a fracture or gradually lengthened to aid in limb lengthening or contraction.

Another aspect of the present invention includes providing an electrical circuit that generates a pulsed current that may travel through two or more pins and which provides an electromagnetic field to the target area of the patient held by the external fixation device. Another aspect of the present invention includes providing at least one electromagnetic transducer coil fixed to the external fixation device to provide an electromagnetic field to the targeted portion of the patient. According to another embodiment of the present invention the electromagnetic coil may be selectively positioned to provide PEMF therapy to the target area of the patient. For example, the electromagnetic coil may be located to provide PEMF therapy to a fracture or to an area of tissue damage. Treating the target area of the patient with the electromagnetic field may increase bone mineral density and stimulate tissue growth. Such an advantage may decrease the time needed for healing.

According to another embodiment of the invention, the apparatus is operable to reduce the likelihood of infection at the patient interface. The device achieves the advantages of using a traditional external fixation device but with a lower risk of complication from infection. For example, the patient interface may be susceptible to osteomylitis or other infections which the present invention may prevent or cure. A further advantage is that the fixation of the electromagnetic transducer coil ensures that the targeted area will routinely receive the desired PEMF treatment.

Additionally, in the event the patient either develops or has a pre-existing infection at or around the patient interface, the tissue/bone growth stimulator may aid in recovery from the infection. Additional technical benefits include increasing the effectiveness of the external fixation device by reducing the risk of pin loosening caused by infection.

Another advantage of the present invention is that therapy may be initiated by a physician and may continue to operate for a predetermined treatment cycle such as four hours per day until removal of the fixation device or change in treatment cycle. As a result further patient or physician intervention may not be required to ensure completion of a treatment cycle once initiated.

Another advantage of the present invention is that the current invention may permit a variety of monitoring activities. For example, the invention may include a window that allows access and/or visual inspection of an osteotomy. In some applications, the window may include materials that do not obstruct one or more imaging wavelengths. For example, the window may include radiolucent material that is relatively transparent to x-rays. Other technical advantages should be readily apparent from the drawing, specification, and claims.

BRIEF DESCRIPTION OF THE DRAWINGS

For a more complete understanding of the present invention, and the advantages thereof, reference is now made to the following brief descriptions taken in conjunction with the accompanying drawings and detailed description, wherein like reference numerals represent like parts, in which:

FIG. 2b is a schematic drawing showing an isometric view of the combined tissue/bone growth stimulator and external fixation device illustrated in FIG. 2a;

FIG. 4b is a schematic drawing showing an isometric view of the combined tissue/bone growth stimulator and external fixation device illustrated in FIG. 4a;

DETAILED DESCRIPTION OF THE INVENTION

Figure 1:
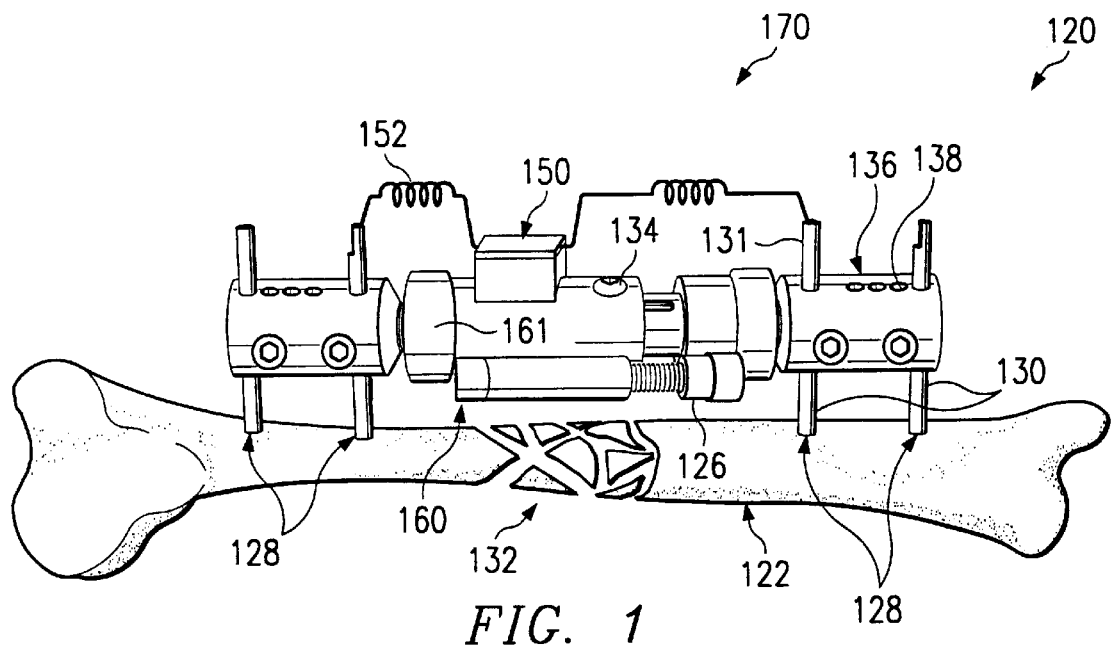
FIG. 1 is a schematic drawing showing an isometric view of a combined tissue/bone growth stimulator and external fixation device incorporating teachings of the present invention.

The preferred embodiments of the present invention and its advantages are best understood by referring to FIGS. 1 through 9b, like numerals being used for like and corresponding parts of the various drawings.

Various embodiments for a combined tissue/bone growth stimulator and external fixation device incorporating teachings of the present invention are shown attached to a long bone 122 of a patient in FIGS. 1, 2b, 3 and 4b. Combined tissue/bone growth stimulator and external fixation devices 120, 220, 320 and 420 may be used in fracture or nonunion management to stimulate bone and/or tissue growth. Combined tissue/bone growth stimulator and external fixation devices 120, 220, 320 and 420 may be used to treat bone fractures, osteotomies, non unions or delayed unions, soft tissue injuries, or reconstructive surgery sites. Uses of combined tissue/bone growth stimulator and external fixation devices 120, 220, 320 and 420 may also include, but are not limited to, procedures such as limb lengthening used to address congenital or traumatic conditions. Other examples may include orthopedic osteotomical procedures such as a high tibial osteotomy (HTO) that may be used to adjust wear patterns for cartilage to delay replacements for a joint.

Satisfactory healing of a fractured bone generally requires reduction and fixation of the bone fracture site. Various types of closed and open reduction techniques may be satisfactorily used to restore overall anatomic alignment of a fractured bone. The fracture surfaces are preferably disposed adjacent to each other and compression preferably provided at the fracture site to increase the area of contact between the fracture surfaces. Ideally, the entire fracture interface will be uniformly compressed. By providing electrical stimulation to the fixation of the bone provided by an external fixation device, combined tissue/bone growth stimulator and external fixation devices 120, 220, 320 and 420 may promote a faster healing rate of bone and/or tissues. Such an advantage may result in more comfort to a patient and reduce healing time.

Combined tissue/bone growth stimulator and external fixation devices 120, 220, 320 and 420 may each be attached to long bone 122 by means of stabilizing devices or pins 130. Combined tissue/bone growth stimulator and external fixation devices 120, 220, 320 and 420 may be disposed substantially externally to the body of the patient(not explicitly shown). Each pin 130 penetrates the body of the patient and is connected to long bone 122 at a corresponding patient interface 128. Combined tissue/bone growth stimulator and external fixation devices 120, 220, 320 and 420 may be attached to long bone 122 to stabilize an area such as an osteotomy, fracture or nonunion 132.

Combined tissue/bone growth stimulator and external fixation devices 120, 220, 320 and 420 each provide a lightweight, simple, and inexpensive approach to treatment in a variety of clinical applications including fracture or osteotomy 132 as illustrated in FIGS. 1–4b. For example, combined tissue/bone growth stimulator and external fixation devices 120, 220, 320 and 420 may be used near bone 122 for the repair of several types of bone injuries or fractures, and/or near any other type of tissue for repair of several types of tissue injuries or surgical procedures. Combined tissue/bone growth stimulator and external fixation devices 120, 220, 320 and 420 may also each attach to bone 122 in osteotomies and/or bone lengthening procedures where at least a portion of bone 122 may be cut or sawed. Combined tissue/bone growth stimulator and external fixation devices 120, 220, 320 and 420 may also be used to promote healing in bones, in connective tissue (such as cartilage and ligaments), as well as to promote nerve regeneration. Fracture or osteotomy 132 is used to illustrate one aspect of the invention.

Combined tissue/bone growth stimulator and external fixation devices 120, 220, 320 and 420 may expedite the healing process when used in place of a cast. For example, combined tissue/bone growth stimulators and external fixation devices 120, 220, 320 and 420 may provide stability and promote tissue growth and/or expedite a rate of healing of the patient in these applications. In some applications, combined tissue/bone growth stimulator and external fixation devices 120, 220, 320 and 420 may also be operable to reduce the risk of or alleviate infection at a patient interface 128.

Galvanic Current Stimulation

Figure 2A:
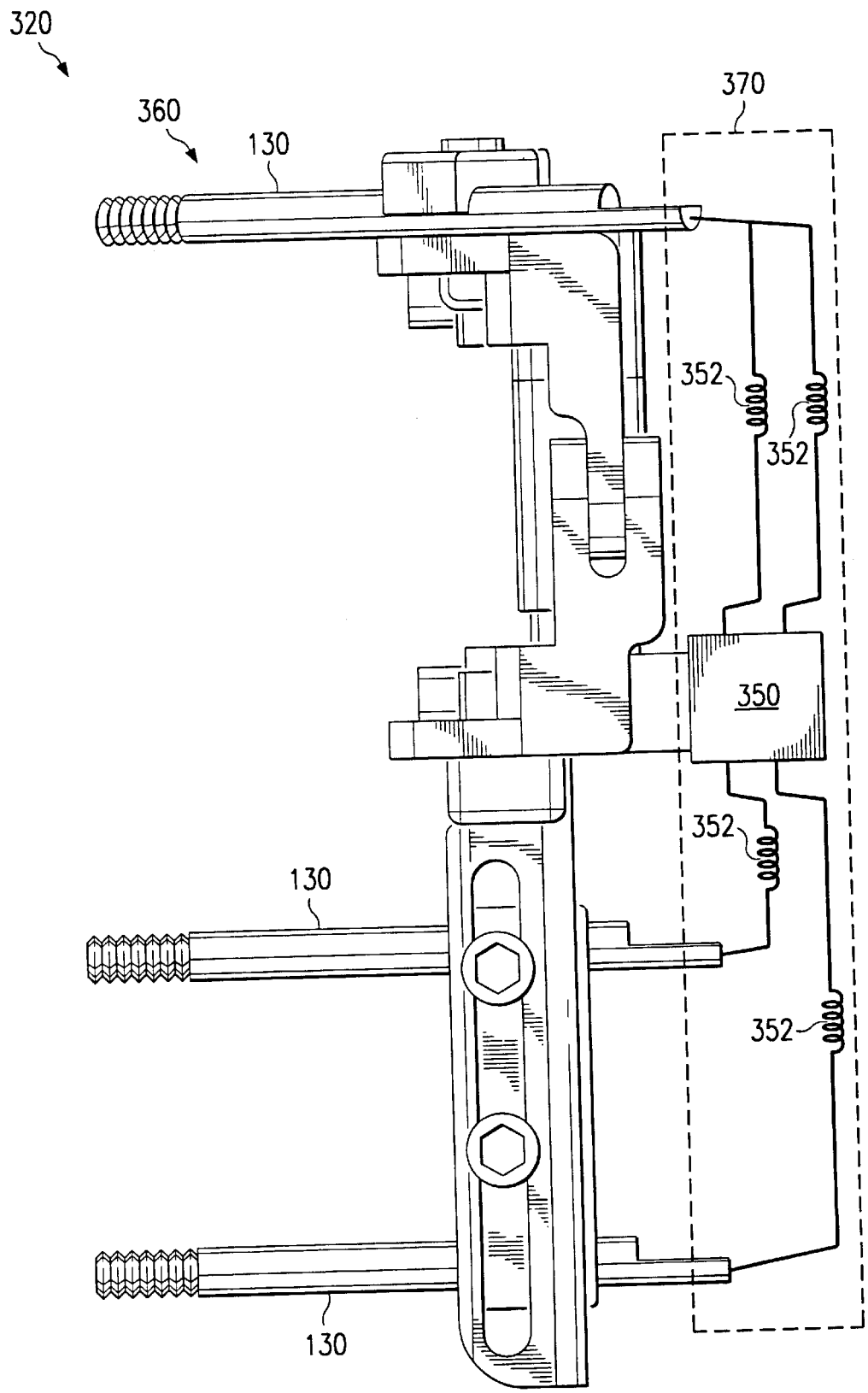
FIG. 2a is a schematic drawing showing a side view of another combined tissue/bone growth stimulator and external fixation device incorporating teachings of the present invention.
Figure 2B:
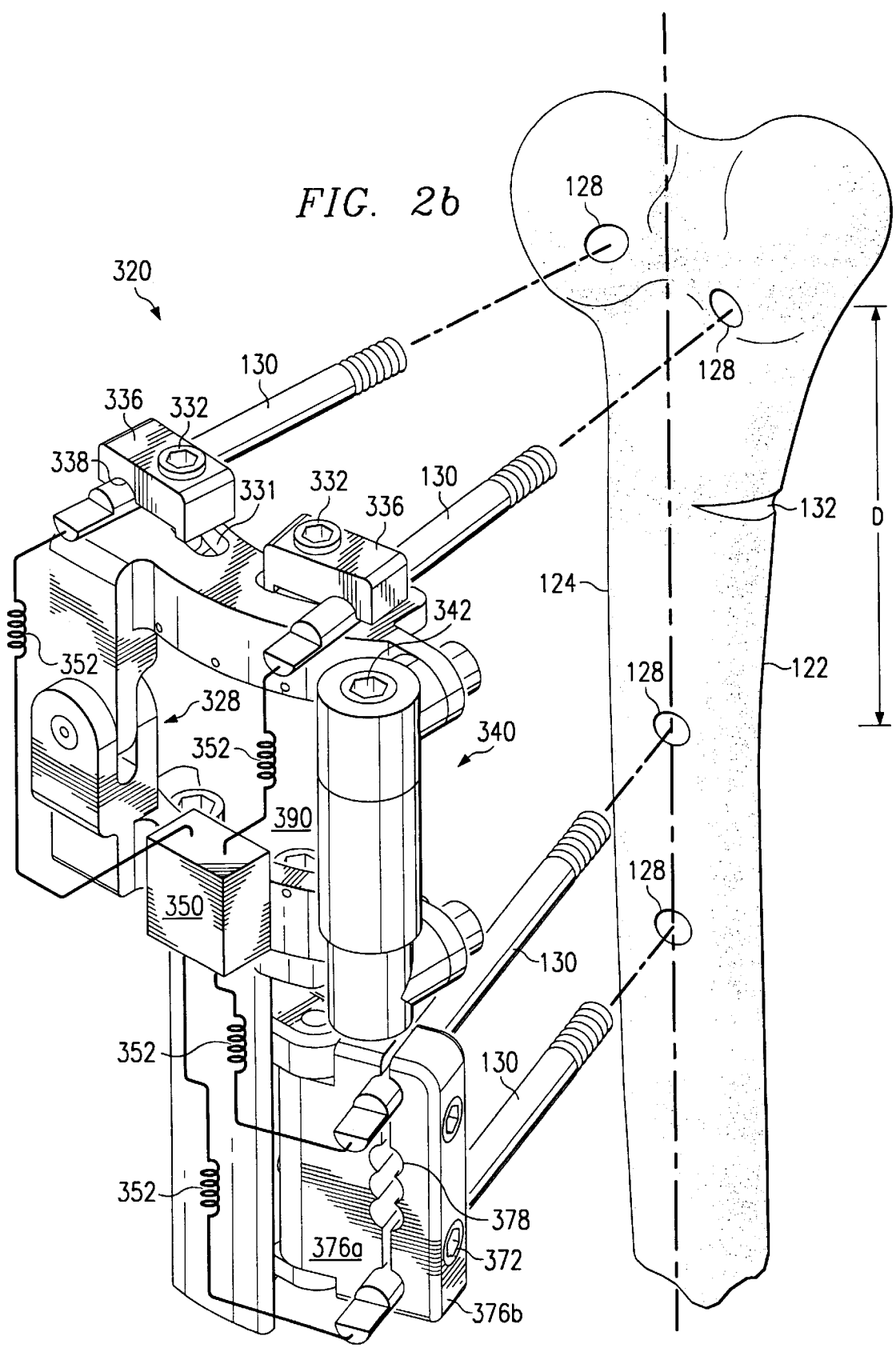

Referring now to FIGS. 1–2b, combined tissue/bone growth stimulator and external fixation devices 120 and 320 are each operable to supply direct current to patient interface 128 by using pins 130 as electrodes. Combined tissue/bone growth stimulator and external fixation device 120 includes a tissue/bone growth stimulator 170 and an external fixation device 160. Similarly, combined tissue/bone growth stimulator and external fixation device 320 includes a tissue/bone growth stimulator 370 and an external fixation device 360.

Pins 130 may be suitably manufactured using implantable grade materials and suitably coated with an electrically non-conductive and compatible material such as parylene so that no portion of conductive material is exposed between patient interface 128 and conductive portion 131 of at least two pins 130. Each of these pins 130 preferably has a portion of conductive material that is exposed generally below patient interface 128.

Tissue/bone growth stimulators 170 and 370 are each operable to provide galvanic, or direct, current through pins 130 to patient interface 128. Use of such direct current may provide the advantage of direct treatment access to corresponding patient interfaces 128 already provided by pins 130. Current may be conducted through an insulating coupler 152 or 352 to one or more nonconductively-coated pins 130 that serve as electrodes. Such direct current travels through pins 130 to corresponding patient interfaces 128 without affecting or dissipating energy to tissues through which pins 130 penetrate. Any configuration of pins 130 may be selected to serve as electrodes. For example, in some applications such as the embodiment depicted in FIG. 2a, two or more pins 130 may be connected to establish a single electrode area. Alternatively or in addition, these selected electrodes may be changed as desired during treatment.

It is also within the scope of the present invention to use implanted electrodes (not explicitly shown) as an alternative to or instead of using pins 130 to deliver current to patient interface 128. For example, separate needle or plate electrodes may be implanted at the treatment site near each patient interface 128. In such an embodiment, these electrodes may be coupled to combined tissue/bone growth stimulator or external fixation devices 120 and 320 by a conductor(not explicitly shown). For example, the conductor may be coupled to electrical circuit within control unit 150 or 350, or to a pin 130. Such a conductor may also be suitably manufactured using implantable grade materials and coated with a material such as parylene to prevent conduction or dissipation of current to other than the treatment site. Use of one or more implantable electrodes may provide more selectively targeted treatment, such as a relatively uniform stimulation along bone 122.

Referring now to FIG. 1, external fixation device 160 includes a number of elements that may be used to releasably connect external fixation device 160 to pins 130. By way of example and not by limitation, external fixation device 160 may include a housing 161 coupled to two clamp mechanisms 136 each operable to secure external fixation device 160 to pins 130. Pins 130 are releasably secured within one of a plurality of slots 138 formed within clamp mechanism 136.

The embodiment of the present invention as shown in FIG. 1 discloses the use of four pins 130. In the embodiment illustrated in FIG. 1, two pins 130 are located below fracture 132, and two pins 130 are located above fracture 132. The present invention contemplates the use of more or fewer pins 130. Pins 130 may be disposed as desired in a variety of configurations around and at a variety of distances from fracture 132. The present invention also contemplates the use of other methods and devices for attaching external fixation device portion 160 to long bone 122. For example, external fixation device portion 160 may be connected to long bone 122 using stabilizing devices including, but not limited to, bone screws, wires, pins or a combination thereof.

External fixation device 160 may be selectively adjusted to treat targeted areas of the patient. By way of example and not by limitation, external fixation device 160 may be selectively expanded or contracted in length in a direction generally parallel to long bone 122. For example, the length of external fixation device 160 may be varied by operating adjustment bolt 126, and may be fixed using set screw 134. Both adjustment bolt 126 and set screw 134 may be coupled to, or form an integral part of, housing 161. In an alternative embodiment, external fixation device 160 may be of a fixed length. In another alternative embodiment, external fixation device 160 may be pivotable. Tissue/bone growth stimulator 170 and external fixation device 160 may also be manufactured as one integrated device.

Tissue/bone growth stimulator portion 170 includes a housing or control unit 150 attached to external fixation device 160 and insulated couplers 152 coupled to pins 130. Control unit 150 may be attached, releasably or otherwise, to housing 161 of external fixation device 160. It is also within the scope of the invention for control unit 150 to be disposed in a variety of configurations that may still provide current to pins 130 while maintaining the operability of external fixation device 160. For example, control unit 150 may be attached to clamp 136, or reside internal to at least a portion of housing 161 of external fixation device 160. Insulated couplers 152 may be any suitably insulated coupler, such as a flexible cable, that is operable to electronically connect control unit 150 to pins 130. Insulated couplers 152, or a portion thereof, may also be similarly disposed within external fixation device 160.

Control unit 150 preferably includes suitable logic and/or electrical circuitry that is operable to send a current signal through at least two pins 130 to treat the patient. The electrical circuitry may include a custom integrated circuit, support elements such as resistors and capacitors to interface to pins 130, a crystal oscillator, and a power source such as a battery. The electrical circuitry may also be powered with any other suitable power source, such as a wall unit. Details for a preferred embodiment of the electrical circuitry in control unit 150 are discussed in conjunction with FIGS. 5a, 5b, and 6.

FIG. 2a is a schematic drawing showing an side view of another combined external fixation device and tissue/bone growth stimulator 320 that is operable to supply direct current to patient interface 128 by using pins 130 as electrodes. Combined tissue/bone growth stimulator and external fixation device 320 includes a tissue/bone growth stimulator 370 and an external fixation device 360. Combined tissue/bone growth stimulator and external fixation device 320 is positioned substantially externally to the body of the patient (not explicitly shown).

FIG. 2b is a schematic drawing showing an isometric view of the combined external fixation device and tissue/bone growth stimulator 320 illustrated in FIG. 2a. Similar to the embodiment discussed previously in conjunction with FIG. 1, external fixation device 360 attaches to long bone 122 at a patient interface 128 by means of four pins 130 above and below osteotomy 132. The embodiment of the present invention as shown in FIG. 2b discloses the use of two proximal pins 130 that are positioned a distance D from two distal pins 130. Fewer or more pins 130 may be used, depending on the application.

External fixation device portion 360 includes a number of elements that may be used to releasably connect external fixation device 360 to pins 130. By way of example and not by limitation, external fixation device 360 may include clamp mechanisms 336 each operable to secure external fixation device 360 to proximal pins 130. Also by way of example and not by limitation, external fixation device 360 includes clamp mechanism 376a and 376b to releasably secure distal pins 130 within a plurality of slots 378 formed within clamp mechanism 376a and 376b. The positions of pins 130 may be selectively adjusted by a variety of mechanisms. For example, clamp mechanisms 336 may be selectively positioned in a slot or track 331 and may be releasably fixed using set screws 332. As discussed in conjunction with the similar elements in FIG. 1, other embodiments for external fixation device 360, pins 130, clamp mechanisms 336, 376a and 376b, slots 331, 338, and 378, and set screws 372 are also within the scope of the invention.

External fixation device 360 may be selectively adjusted to treat targeted areas of the patient. For example, external fixation device 360 may be used to angulate bone 122 to provide, for example, valgus and/or varus correction. External fixation device 360 includes a window 390 formed and enclosed by an angulation and adjustment portion 340. Window 390 provides an unobstructed view of long bone 122 that desirably allows examination of and/or access to osteotomy 132. Window 90 is enlarged as external fixation device 360 is adjusted.

By way of example and not by limitation, window 390 may be selectively expanded by rotation about hinge 328 to angulate tibia 122. In this embodiment, angulation adjustment portion 340 may be slightly rotated while proximal and distal pins 130 maintain positioning of combined tissue/bone growth stimulator and external fixation device 320 in tibial bone 122 as length D is increased. A variety of techniques may be used to increase length D. The present invention also contemplates the use of other hingeable, pivotable or rotatable means to expand window 390.

Window 390 preferably allows the physician and/or the patient to palpitate, visually inspect and/or monitor healing of the wound created by osteotomy 132 therethrough. In addition, window 390 permits an unobstructed view of osteotomy 132 and surrounding bone and/or other tissue for a variety of examination and monitoring procedures. Such an advantage allows a variety of examination techniques to be used to observe the healing processes of osteotomy 132 and/or valgus and/or varus correction of bone 122 during treatment while window 390 is enlarged. For example, procedures including, but not limited to, radiographic and ultrasonic imaging may be used to capture unobstructed views of bone 122 and surrounding tissues at a variety of points during the healing process as bone 122 is angulated.

In some applications, it may be desirable for some or all of the elements within angulation adjustment portion 340 to be manufactured using a variety of composite materials. For example, those elements forming and enclosing window 390 may include radiolucent materials that are transparent to x-ray wavelengths. Such an embodiment provides the advantage of a larger unobstructed imaging area through which a physician may obtain images to analyze the healing process.

Tissue/bone growth stimulator portion 370 includes a housing or control unit 350 attached to external fixation device 360 and insulated couplers 352 coupled to pins 130. Control unit 350 may be attached, releasably or otherwise, to external fixation device 360. In the embodiment illustrated in FIG. 2b, control unit 350 is attached to angulation adjustment portion 340. It is also within the scope of the invention for control unit 350 to be disposed within or attached to external device 360 in a variety of configurations that may still provide current to pins 130 while maintaining the operability of external fixation device 360. In some applications, it may be desirable to releasably attach all or some portions of tissue/bone growth stimulator portion 370 to external device 360 so that it may be removed while performing imaging examinations.

Similar to the embodiment illustrated in FIG. 1, control unit 350 includes suitable logic and/or electrical circuitry that is operable to send a current signal through at least two pins 130 to treat the patient. In this embodiment, four insulated couplers 152 electronically connect control unit 350 to two proximal pins 130 and to distal pins 130. Details for a preferred embodiment of the electrical circuitry in control unit 350 are discussed in conjunction with FIGS. 5a, 5b, and 6.

Insulated couplers 352 may be any suitably insulated coupler, such as a flexible cable, that is operable to electronically connect control unit 350 to pins 130. In this embodiment, insulated couplers 352 are coupled to two proximal pins 130 and two distal pins 130 to treat the entire area between the four pins 130. In addition, such an embodiment may stimulate bone and/or tissue growth at patient interface 128 around all four pins. In other applications, it may be desirable to couple insulated couplers 352 to fewer or more pins 130. Insulated couplers 352 may be desirably sized to accommodate an increase in distance D between proximal and distal pins 130, as external fixation device 360 is extended to angulate bone 122.

In operation for both embodiments discussed in conjunction with FIGS. 1–2b, a pulsed current is generated, the current flows through at least two pins 130, and an electromagnetic field is created. For example, the pulsed current may be a switched DC current that is sent from the electrical circuitry through at least two pins 130. The electromagnetic field penetrates a desired targeted area created between the pins 130 through which current flows. The electromagnetic field is created in a treatment volume that may be considered to generally extend a radial distance from the current flowing between two pins 130 through the patient. The electromagnetic field may also be created in a treatment volume at or near patient interface 128. Such an electromagnetic field created by a pulsed current source is similar at the tissue and cellular level to one induced by a PEMF device. Thus, combined tissue/bone growth stimulator and external fixation devices 120 and 320 may be used to deliver a non-invasive, low-energy, electromagnetic field to a targeted treatment site or sites of the patient. For example, tissue/bone growth stimulators 170 or 370 could be suitably coupled to selectively positioned pins 130 to provide galvanic current to the area of fracture or osteotomy 132, and/or to an area of tissue damage.

In operation, combined tissue/bone growth stimulator and external fixation devices 120 and 320 may be used for a period of time suitable for healing. A physician may provide a treatment plan that includes continuous treatment or treatment at various intervals. For example, a patient may utilize combined tissue/bone growth stimulator and external fixation devices 120 and 320 for a time of between two and eight hours. It may be particularly advantageous for the patient to use combined tissue/bone growth stimulator and external fixation devices 120 and 320 for a continuing treatment time of four hours.

Combined tissue/bone growth stimulator and external fixation devices 120 and 320 may also automatically provide a preset amount of daily treatment, or may be started and stopped by a patient. In some applications, combined tissue/bone growth stimulator and external fixation devices 120 and 320 may be operable to turn itself off at the end of the preset amount of treatment in a day.

In operation, tissue/bone growth stimulators 170 and 370 may utilize any suitable frequency and waveform characteristics to stimulate bone and/or tissue growth. Because bone growth is responsive to the harmonic content of signals, it may be advantageous to use pulse or square waveforms. These waveforms, including periodic repeatable waveforms, include a suitable variety of different frequencies. The duration, amplitude, and frequency of each waveform may also include any suitable values that are conducive to stimulation of bone and/or tissue growth. For example, it may be desirable to utilize a selected or adaptive minimum and/or maximum threshold for waveform amplitude. In some applications, it may be desirable to induce electrical fields of approximately 3 mv/cm for a positive pulse portion and 1 mv/cm for a negative pulse portion by utilizing power levels such as 2.1 mA and 700 $\mu$A for each respective portion. The electrical fields and power levels may vary depending on the application. Examples of signals that may be produced by tissue/bone growth stimulators 170 and 370 are described and discussed in conjunction with FIGS. 9a and 9b.

Transducer Coil Stimulation

Figure 3:
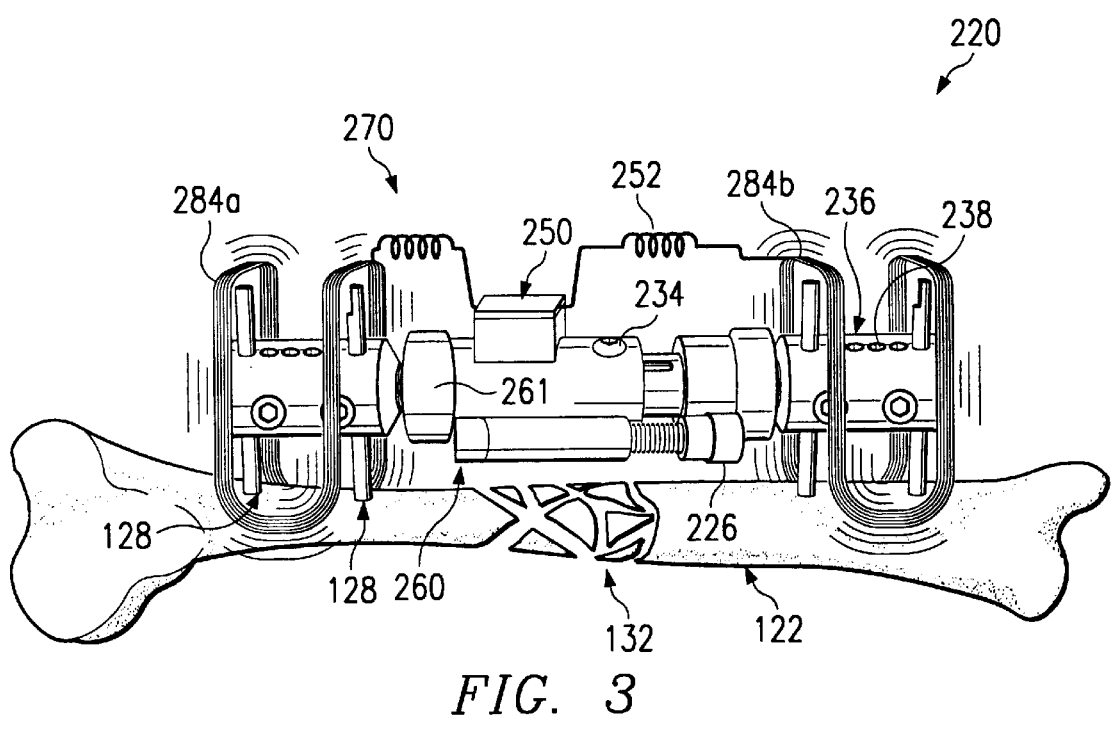
FIG. 3 is a schematic drawing showing an isometric view of another combined tissue/bone growth stimulator and external fixation device incorporating teachings of the present invention.
Figure 4A:
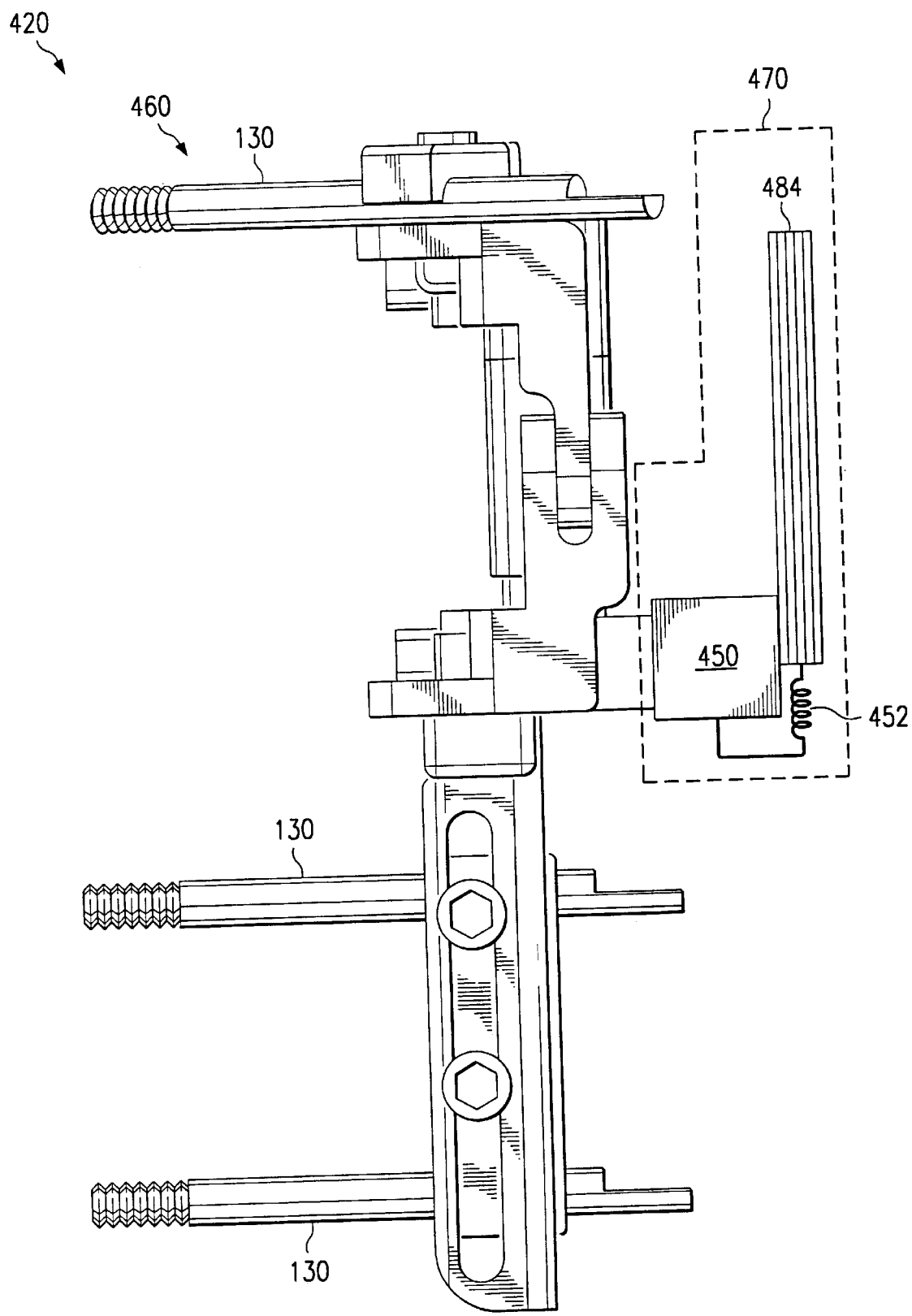
FIG. 4a is a schematic drawing showing a side view of another combined tissue/bone growth stimulator and external fixation device incorporating teachings of the present invention.
Figure 4B:
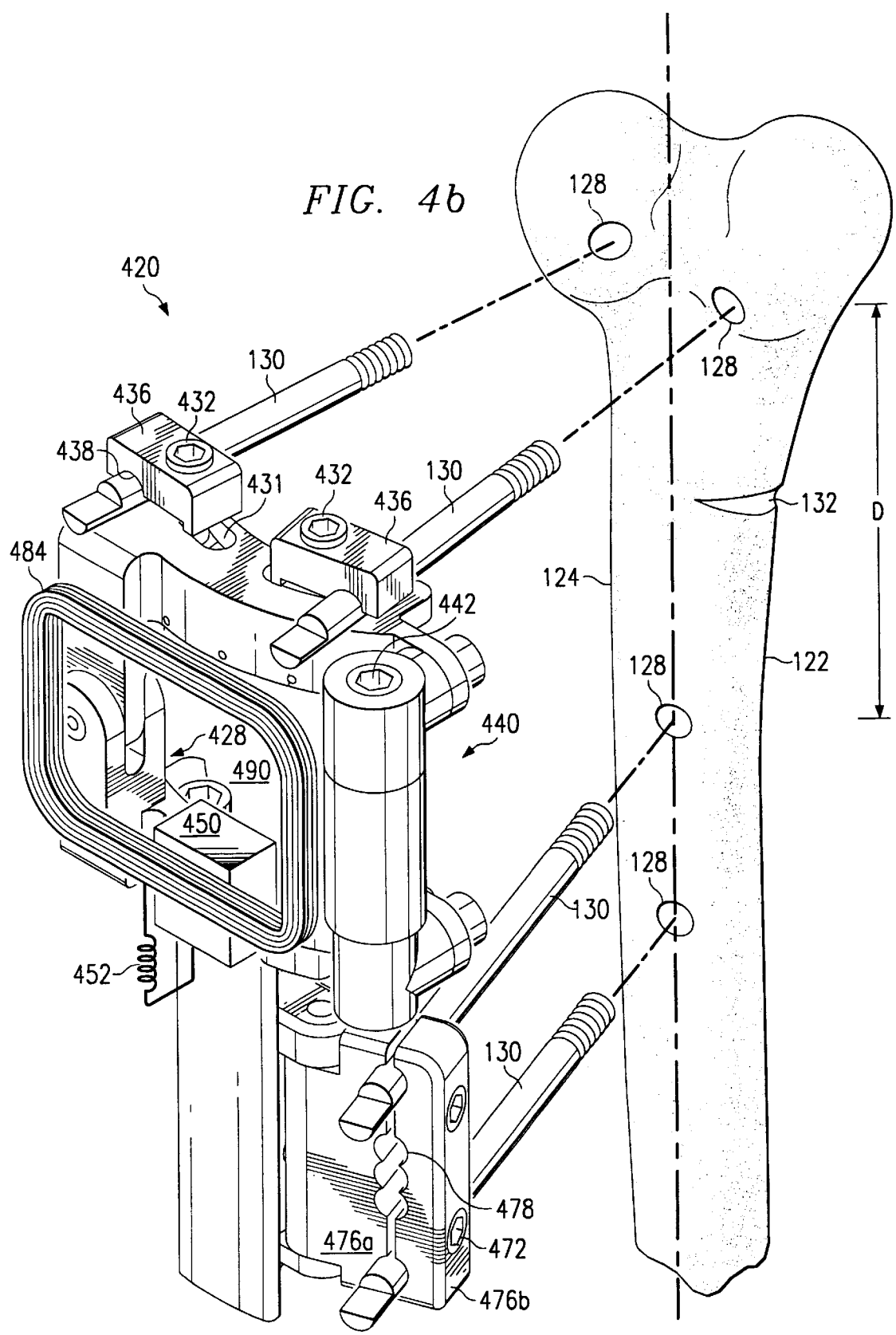

Referring now to FIGS. 3–4b, in operation, the embodiments of the present invention disclose a combined tissue/bone growth stimulator and external fixation device 220 and 420 that may produce electrical signals similar to Physio-Stim® Lite or Spinal-Stim® Lite devices that are offered by Orthofix. Examples of signals that may be associated with combined tissue/bone growth stimulator and external fixation device 220 and 420 are illustrated and discussed in conjunction with FIGS. 9a and 9b.

Similar to the embodiments illustrated in FIGS. 1 and 2, combined tissue/bone growth stimulator and external fixation devices 220 and 420 may provide stability and promote tissue growth and/or expedite a rate of healing of the patient. In some applications, combined tissue/bone growth stimulator and external fixation devices 220 and 420 may also be operable to reduce the risk of or alleviate infection at patient interface 128.

FIG. 3 is a schematic drawing showing an isometric view of another combined external fixation device and tissue/bone growth stimulator 220 incorporating teachings of the present invention.

In this embodiment, combined tissue/bone growth stimulator and external fixation device 220 includes a tissue/bone growth stimulator portion 270 and an external fixation device portion 260. Similarly to the embodiment discussed previously in conjunction with FIG. 1, external fixation device 260 attaches to long bone 122 at a patient interface 128 by means of a plurality of pins 130 in the proximity of fracture 132. Fewer or more pins 130 may be used, and at suitable locations near fracture 132, depending on the application. External fixation device 260 also includes clamp mechanism 236, slots 238, adjustment bolt 226 and set screw 234, and may be similarly adjusted as discussed above in conjunction with clamp mechanism 136, slots 138, adjustment bolt 126 and set screw 134 as shown in FIG. 1. As similarly discussed in conjunction with these same elements in FIG. 1, other embodiments for external fixation device 260, pins 130, clamp mechanism 236, slots 238, adjustment bolt 226 and set screw 234 are also within the scope of the invention.

Tissue/bone growth stimulator portion 270 is secured to external fixation device 260 at housing 261, and is operable to supply PEMF at the patient interface 128. Tissue/bone growth stimulator 270 and external fixation device 260 may also be manufactured as one integrated device.

In this embodiment, tissue/bone growth stimulator 270 includes two transducer coils designated 284a and 284b disposed generally at each end of external fixation device 260. In operation, tissue/bone growth stimulator 270 includes a housing or control unit 250 that preferably sends programmed electrical impulses to transducer coils 284b and 284a. Transducer coils 284b and 284a, in turn, develop a PEMF. Thus, when combined tissue/bone growth stimulator and external fixation device 220 is secured to the patient, transducer coils 284b and 284a deliver a non-invasive, low-energy, PEMF to a selected treatment site or sites of the patient.

Control unit 250 is shown secured to housing 261 of external fixation device 260. Insulated couplers 252 may be any suitable couplers, such as flexible cables, that electrically connect control unit 250 with transducer coils 284a and 284b. Similarly as discussed with regard to control unit 150 as shown in FIG. 1, in some applications control unit 250 may be disposed within housing 261.

It is also within the scope of the invention for any number of transducer coils (not expressly shown) to be operated by control unit 250. For example, tissue/bone growth stimulator 270 may include a single transducer coil secured to housing 261 of external fixation device 260. Alternatively, tissue/bone growth stimulator 270 may include a plurality of transducer coils secured to housing 261 that may be, for example, oriented relatively parallel to bone 122. This plurality of transducer coils may provide PEMF to treat the area along bone 122. Additional transducer coils may also be configured to treat specific portions of a patient's body such as patient interface 128, or other soft tissue areas for which such treatment is desirable. In another alternative embodiment, tissue/bone growth stimulator 270 may be selectively movable to allow for increased precision and flexibility in targeting a area of treatment. For example, one or more transducer coils may be slidably or pivotably secured to housing 261 and adjusted as desired. As another example, tissue bone growth stimulator 270 can be formed to the anatomical contour of the targeted area and releasably fixed.

FIG. 4*a* is a schematic drawing showing a side view of another combined tissue/bone growth stimulator and external fixation device incorporating teachings of the present invention. Combined tissue/bone growth stimulator and external fixation device 420 includes a tissue/bone growth stimulator 470 and an external fixation device 460. Combined tissue/bone growth stimulator and external fixation device 420 is positioned substantially externally to the body of the patient (not explicitly shown).

FIG. 4*b* is a schematic drawing showing an isometric view of the combined external fixation device and tissue/bone growth stimulator 420 illustrated in FIG. 4*a*. Similar to the embodiment discussed previously in conjunction with FIGS. 2*a* and 2*b*, external fixation device 460 attaches to long bone 122 at a patient interface 128 by means of four pins 130 above and below osteotomy 132. Fewer or more pins 130 may be used, depending on the application.

External fixation device portion 460 includes a number of elements that may be used to releasably connect external fixation device 460 to pins 130. Similarly to the embodiment discussed previously in conjunction with FIGS. 2*a* and 2*b*, external fixation device 460 includes clamp mechanisms 436, 476*a* and 476*b* slots 431, 438 and 478, and set screws 472 and 482. As discussed in conjunction with the similar elements in FIGS. 2*a* and 2*b*, other embodiments for external fixation device 460, pins 130, clamp mechanisms 436, and 476*a* and 476*b*, slots 431, 438, and 478, and set screws 472 and 482 are also within the scope of the invention.

Also as discussed in conjunction with the similar elements in FIGS. 2*a* and 2*b*, external fixation device 460 includes a window 490 formed and enclosed by an angulation adjustment portion 440. Window 490 provides an unobstructed view of long bone 122 that desirably allows examination of and/or access to osteotomy 132. Window 490 is enlarged as external fixation device 460 is adjusted.

Window 490 preferably allows the physician and/or the patient to palpitate, visually inspect and/or monitor healing of the wound created by osteotomy 132 therethrough. In addition, window 490 permits an unobstructed view of osteotomy 132 and surrounding bone and/or other tissue for a variety of examination and monitoring procedures. For example, window 490 may obstruct fewer signals from tissue/bone growth stimulator portion 470 than conventional devices.

As another example, procedures including, but not limited to, radiographic and ultrasonic imaging may be used to capture unobstructed views of bone 122 and surrounding tissues at a variety of points during the healing process as bone 122 is angulated. Such an advantage allows a variety of examination techniques to be used to observe the healing processes of osteotomy 132 and/or valgus and/or varus correction of bone 122 during treatment while window 490 is enlarged.

Similar to the embodiment illustrated in FIG. 3, tissue/bone growth stimulator portion 470 includes a housing or control unit 450 attached to a single transducer coil 484 by an insulated coupler 452. Control unit 450 is attached to external fixation device 460 and is operable to supply PEMF at the patient interface 128. Tissue/bone growth stimulator 470 and external fixation device 460 may also be manufactured as one integrated device. In this embodiment, tissue/bone growth stimulator 470 includes transducer coil 484 that may conform generally with the shape of window 490. In operation, tissue/bone growth stimulator 470 includes a housing or control unit 450 that preferably sends programmed electrical impulses to transducer coil 484, which, in turn, develops a PEMF. Thus, when combined tissue/bone growth stimulator and external fixation device 420 is secured to the patient, transducer coil 484 delivers a non-invasive, low-energy, PEMF to a selected treatment site or sites of the patient.

Transducer coil 484 may be sized large enough to accommodate any enlargement in window 490. In some applications, it may be desirable for some or all of the elements within angulation adjustment portion 440 to be manufactured using a variety of composite materials such as radiolucent materials that are transparent to X-ray wavelengths. Alternatively or in addition, tissue/bone growth stimulator 470 may be releasably coupled to external fixation device for removal during imaging examinations. Such embodiments may provide the advantage of a larger unobstructed imaging area through which a physician may obtain images to analyze the healing process.

Insulated coupler 452 may be any suitable coupler, such as a flexible cable, that electrically connects control unit 450 with transducer coil 484. It is also within the scope of the invention for any number of transducer coils (not expressly shown) to be operated by control unit 450. For example, tissue/bone growth stimulator 470 may include a plurality of transducer coils secured to external fixation device 460 that may be, for example, oriented relatively parallel to bone 122. This plurality of transducer coils may provide PEMF to treat the area along bone 122. Additional transducer coils may also be configured to treat specific portions of a patient's body such as patient interface 128, or other soft tissue areas for which such treatment is desirable. In another alternative embodiment, tissue/bone growth stimulator 470 may be selectively movable to allow for increased precision and flexibility in targeting a area of treatment. For example, one or more transducer coils may be slidably or pivotably secured to clamps 436 and adjusted as desired. As another example, tissue bone growth stimulator 470 can be formed to the anatomical contour of the targeted area and releasably fixed.

Each of transducer coils 284*a*, 284*b* and 484 may be suitably sized and located to provide PEMF at a targeted area of the patient. The configuration of these transducer coils along with electrical drive signals provided by control unit 250 or 450 through insulated couplers 252 or 452, respectively, are preferably selected to provide a relatively uniform magnetic field and relatively constant peak flux densities throughout a desired treatment volume. For example, transducer coils 284*a* and 284*b* may each encompass fracture 132 and/or an area of tissue damage with a desired penetration shadow, or coverage area.

The size and configuration for these transducer coils may also vary widely depending on the application. For example, larger coils may be used to treat larger areas such as those that include a femur bone. Each transducer coil may also be wound in a variety of configurations, depending on the nature of the clinical application and/or treatment site. For example, it may be advantageous to treat an area including a femur bone by using a single transducer coil 284a or 484 having approximately a four inch radius and height. On the other hand, a smaller area, such as that including a tibial bone, may be suitably treated using a three inch coil. As another example, one or more transducer coils 284a, 284b and/or 484 could be positioned to provide PEMF at or near fracture or osteotomy 132, and/or to an area of tissue damage. In some applications, it may also be advantageous for coils to be disposed near pins 130 to, for example, prevent pins 130 from loosening and/or to prevent infection.

In addition, these transducer coils may include a single set of primary windings, or two or more primary windings in parallel layered on top of each other. Transducer coils 284a, 284b, and 484 may be formed from commercially available eighteen gauge wire. In one embodiment, transducer coils may be wound according to the winding schedule: 1 layer×5 turns×20 American Wire Gauge (AWG) and each have a resistance of 0.32 ohms and an inductance of 25.4 $\mu$H. For some applications, control unit 250 or 450 may be powered by a standard power source such as a wall unit. In this embodiment, transducer coils 284a, 284b, and 484 may be wound according to a different winding schedule, for example, 2 layers×7 turns×20 AWG.

In operation, similar to the embodiments discussed in conjunction with FIGS. 1–2b, a patient may use combined tissue/bone growth stimulator and external fixation devices 220 and 420 for a treatment time lasting for a time of between two and eight hours. It is often particularly advantageous for the patient to a continuing treatment time of four hours. The patient may turn on and off combined tissue/bone growth stimulator and external fixation devices 220 and 420. Alternatively or in addition, control unit 250 or 450 may provide a preset amount of daily treatment and may be operable to turn itself off at the end of the preset amount of treatment in a day.

Control unit 250 may also include circuitry, such as one or more ON/OFF switches, to control the operation of either or both transducer coils 284a and 284b. Similarly, control unit 450 may include circuitry, such as an ON/OFF switch, to control the operation of transducer coil 484. In some applications, control unit 250 or 450 may also include additional controls (not explicitly shown) for controlling treatment information access. Control unit 250 or 450 may also provide an alarm function and/or a number of indicator lights, such as light emitting diodes (LEDs), to indicate operational status such as when treatment is in process, when treatment has been completed if a battery power source is low. Control unit 250 or 450 may be powered by any suitable battery or other standard power source. For some applications, control unit 250 or 450 may contain a single nine (9) volt disposable lithium battery (not expressly shown).

Electrical circuitry that may be disposed within control unit 250 or 450 may provide a pulsing bi-phasic current to respective transducer coils at predetermined intervals, thereby activating the PEMF output signal according to a prescribed pre-programmed PEMF regimen. Except for transducer coils 284a and 284b, this circuitry may be physically located in control unit 250, and except for transducer coil 484, this circuitry may be physically located in control unit 450. The electrical circuitry may include both control circuitry, field sense circuitry and drive circuitry, which all may be fabricated on a printed circuit board and encapsulated in control unit 250 or 450. One embodiment for such circuitry is discussed in conjunction with FIGS. 7–8b.

Figure 5A:
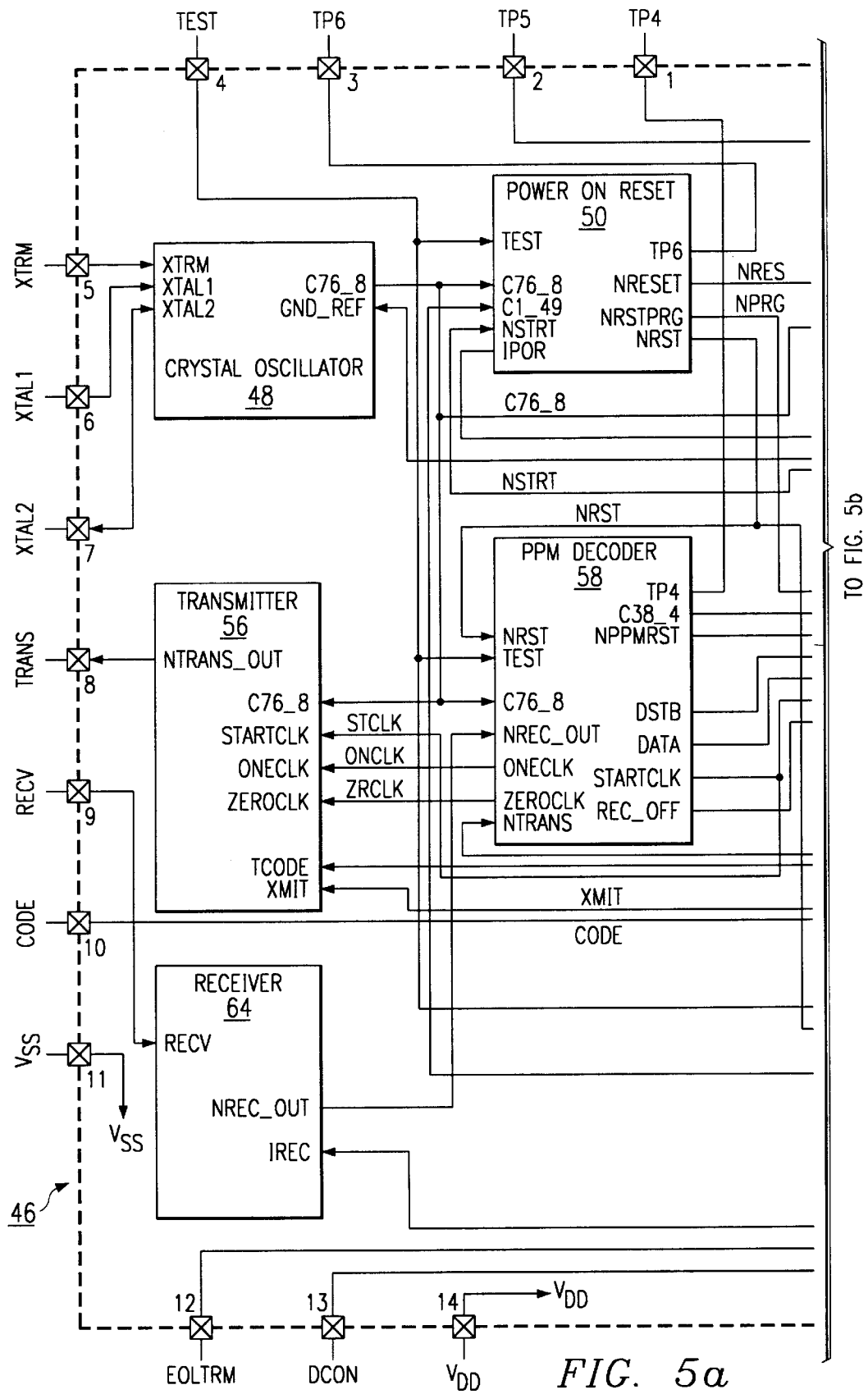
FIGS. 5a and 5b illustrate schematically electrical circuitry that may be used in the combined tissue/bone growth stimulator and external fixation devices depicted in FIGS. 1–2b.
Figure 5B:
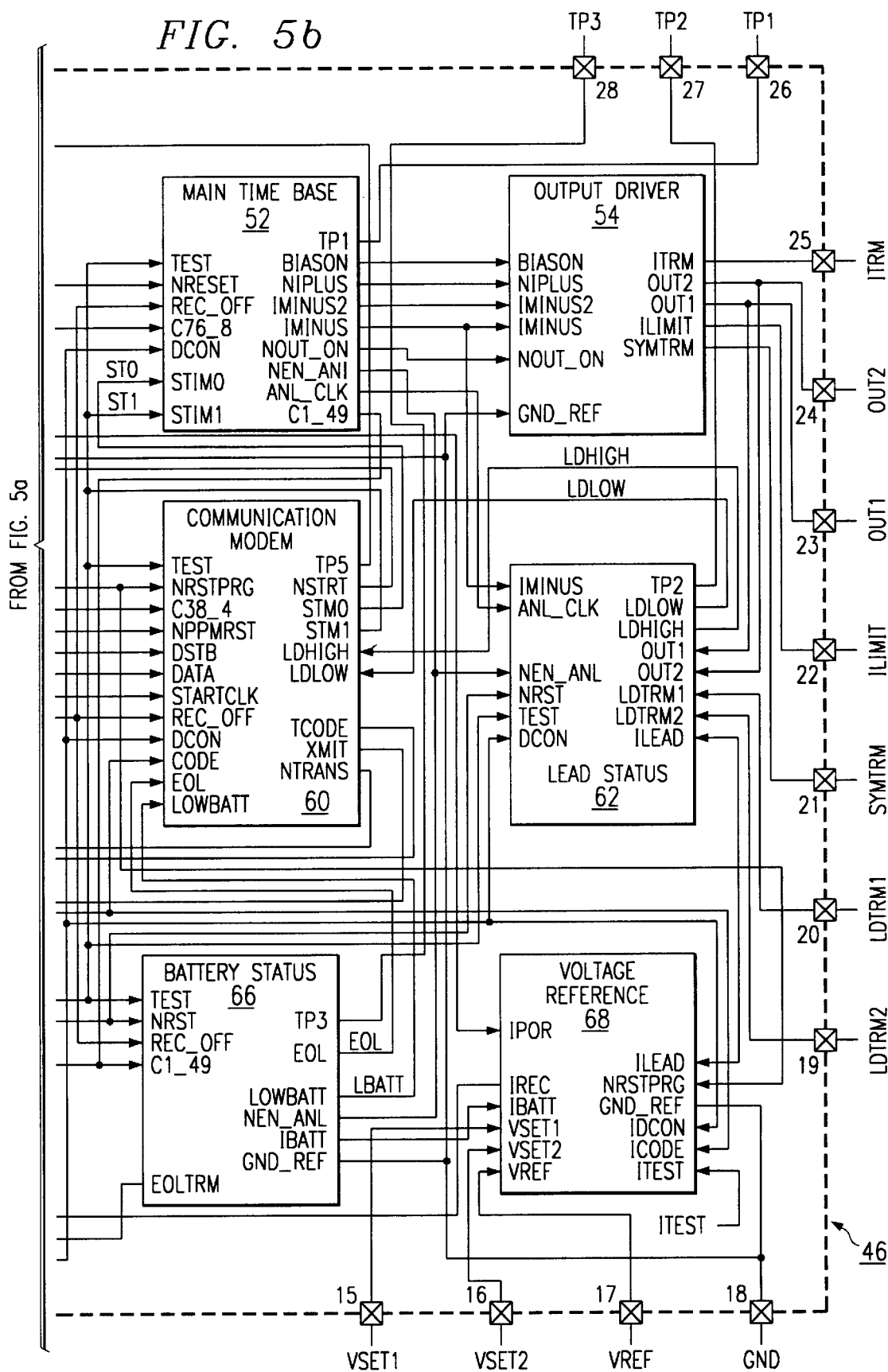

FIGS. 5a and 5b illustrate schematically electrical circuitry that may be used in the combined tissue/bone growth stimulator and external fixation devices depicted in FIGS. 1–2b. The electrical circuitry includes an application specific integrated circuit 46 that may be packaged in a variety of ways, including on a substrate, a printed circuit board, or externally packaged as a part of in housing 161. The electrical circuitry preferably provides a pulsed galvanic current (switched DC) to pins 130, which generates an electromagnetic field internal to the patient. In one embodiment, a DC current may be provided by utilizing a suitable current regulator. The electrical circuitry may be powered with any suitable power source, such as a battery or wall unit.

The electrical circuitry may also be used with an external receiver. This external receiver may be a mobile or stationary device operable to program, monitor and/or control combined tissue/growth stimulator and external fixation device 120. In some applications, it may be desirable to wirelessly uplink and downlink information between the external receiver and integrated circuit 46 using, for example, an infrared or radio frequency link. Such an advantage may enhance the mobility of a patient receiving treatment. Other wireless or direct communication links are also within the scope of the invention.

The following signals may be used by an integrated circuit 46 internally and as external connections:

ANL_CLK is generated by main time base circuit 52. It enables lead status circuit 62 during certain intervals of the DC output signal.

BIASON is generated by the main time base circuit 52. In the AC mode, it turns on the bias current for the positive portion of the output signal. It is disabled during the negative portion of the AC signal output. BIASON is used by the output driver.

C1_49 is generated by main time-base circuit 52. One example signal may be a clock signal of 1.49 Hz. It is used as a gating signal for the control logic of the output switches of output driver 54.

C76_8 is generated by crystal oscillator circuit 48. One example signal may be a clock signal of 76.8 kHz. It is the main time signal used by integrated circuit 46.

CODE is an externally hardwired input bit (Pad 10). The communication protocol requires that communication words have a matching bit for a valid downlink.

DATA is generated by PPM decoder block 58. One example signal may be the output from the PPM decoder indicating a valid data 0 or data 1 received from receiver circuit 64.

DCON is an externally hardwired bit (Pad 13). It is used to indicate for which configuration, AC or DC, the circuit is set up. A logic level of 0 indicates an AC configuration while logic level 1 indicates a DC configuration.

DSTB is generated by PPM decoder circuit 58. It strobes valid data into communication modem circuit 60.

EOL is generated by battery status circuit 66. For example, this bit will have a logic value of 1 when the battery voltage is less than or equal to 2.1 V. Otherwise it will have a logic value of 0.

EOLTRM is an input to battery status circuit 66. It may be coupled to $V_{DD}$ through an external capacitor and resistor (Pad 12). It is used to trim the low battery and end of life voltages to the desired trip points (here, 2.4 and 2.1 V respectively).

GND_REF is generated by voltage reference/regulator circuit 68. One example signal may be a buffered voltage level, 1.5 V less than $V_{DD}$. It is brought off-chip through pad 18.

IBATT is generated by voltage reference regulator circuit 68. One example signal may produce a 20 nA current sink used to establish the bias current in battery status circuit 68.

ICODE is generated by the voltage reference/regulator circuit 68. One example signal may produce a 100 nA current sink used to pull down the CODE pin if that pin is left open.

IDCON is generated by voltage reference/regulator circuit 68. One example signal may produce a 100 nA current sink used to pull down the DCON pin if that pin is left open.

ILEAD is generated by voltage reference/regulator circuit 68. One example signal may be a 20 nA current source used to bias lead status circuit 62.

ILIMIT is an external connection to output driver circuit 54 (Pad 22). In the AC mode, ILIMIT is not used. In the DC mode, ILIMIT is connected to the stimulator housing and acts as the unit anode.

IMINUS is generated by main time base circuit 52. In the AC mode, it switches the negative output portion of the signal. In the DC mode, it switches the output current. It is used by output driver circuit 54.

IMINUS2 is generated by main time base circuit 52. In the AC mode, it is not used. In the DC mode, it switches the output current for OUT2. It is used by output driver circuit 54.

IPOR is generated by voltage reference/regulator 68. One example signal may be a 10 nA current sink used to bias the power on reset circuit 50.

IREC is generated by voltage reference/regulator 68. One example signal may be a 20 nA current source used by the receiver circuit 64.

ITEST is generated by the voltage reference/regulator 68. One example signal may be a 100 nA current sink used to pull down the TEST pin if that pin is not connected.

ITRM is an external connection to $V_{DD}$ through an external resistor (Pad 25). The resistor is used to trim the output current in both the AC and DC modes. It is an input to output driver circuit 54.

LDHIGH is generated by the lead status unit. In the AC mode, a logic level 1 indicates a high lead impedance. In the DC mode, a logic level 1 indicates a high lead impedance for OUT2.

LDLOW is generated by the lead status unit. In the AC mode, a logic level of 1 indicates a low lead impedance. In the DC mode, logic level of 1 indicates a high lead impedance for OUT1.

LDTRM1 is an input to lead status circuit 62. It may be coupled to GND_REF through an external resistor (Pad 20). It sets the trip points for lead status circuit 62.

LDTRM2 is an input to lead status circuit 62. It is coupled to GND_REF through two resistors in series (Pad 19). It is used to set the trip points for lead status circuit 62.

LOWBATT is generated in battery status circuit 66. This signal is normally low. When the battery output drops below 2.4 V, this signal switches to logic level 1.

NEN_ANL is generated by main time base unit 52. In the AC mode, this signal enables the battery and lead status circuits during the negative portion of the output signal. Otherwise, these circuits may be disabled to conserve power.

NIPLUS is generated by main time base circuit 52. In the AC mode, this signal controls the output switch for the positive portion of the output signal.

NOUT_ON is generated by main time base circuit 52. In the AC mode, this signal enables the output driver during the burst period. It is otherwise off.

NPPMRST is generated by PPM decoder circuit 58. It is a primary reset for the communication modem circuit 60.

NREC_OUT is generated by the receiver circuit 64. It is a digital representation of the received external input.

NRESET is generated by power on reset circuit 50. It is reset on power up and after a valid downlink/uplink communication. In either case, it returns high after, for example, two 76.8 kHz clock cycles.

NRST is generated by power on reset circuit 50. It is reset on power up and after a valid downlink/uplink communication. In either case, it returns to its high state after, for example, one 1.49 Hz clock cycle.

NRSTPRG is generated by power on reset circuit 50. It is reset on power up. It returns to its high state after NRST transitions high.

NSTRT is generated by communication modem circuit 60. It initiates a reset after a valid downlink/uplink communication.

NTRANS is generated by communication modem circuit 60. It indicates the completion of a valid downlink communication.

NTRANS_OUT is generated by transmitter unit 58. It is the output signal of the driver stage of the transmitter circuit 56. It is connected to an external coil (Pad 8).

ONECLK is generated by PPM decoder circuit 58. It is the decoded clock signal corresponding to the data position for logic level one in the communications protocol.

OUT1 is an output from output driver circuit 54 (Pad 23). In the both the AC and DC modes, this is the output signal.

OUT2 is an output from output driver circuit 54 (Pad 24). In the AC mode, OUT2 is connected to OUT1.

REC_OFF is generated by PPM decoder circuit 58. This signal disables the receiver, battery status and output driver circuits during an uplink operation.

RECV is input to receiver unit 56. It is coupled to an external coil (Pad 9).

STARTCLK is generated by PPM decoder circuit 58. It is a decoded clock signal corresponding to the start position in the communications protocol.

STIM0 is generated by communication modem circuit 60. It is used with the STIM1 bit to generate the four stimulation modes (off, on 4 hours, on 8 hours, on continuously).

STIM1 is generated by communication modem circuit 60. It is used with the STIM0 signal to generate the four stimulation modes (off, on 4 hours, on 8 hours, on continuously).

SYMTRM is an input to output driver circuit 54. It may be coupled to GND_REF or $V_{DD}$ through an external resistor (Pad 21). It is used to trim the positive portion of the output current. It is presently not used.

TCODE is generated by communication modem circuit 60. It is the data output sent to transmitter circuit 56 for external transmission.

TEST is a testing signal used in conjunction with TP1 through TP6. It is brought off chip at pad 4.

TP1 through TP6 are external test points (Pads 26, 27, 28, 1, 2, and 3 respectively). They output data from the various cell blocks for testing purposes.

$V_{DD}$ is an external connection to the positive terminal of the 2.8 V battery (Pad 14).

$V_{SS}$ is an external connection to the negative terminal of the 2.8 V battery (Pad 11).

VREF is an input to voltage reference/regulator circuit 68. It may be coupled to a 1.5 V unbuffered reference voltage (Pad 17).

VSET1 is an input to voltage reference/regulator circuit 68. It is coupled to $V_{DD}$ through two external resistors in series (Pad 15). It is used to trim VREF.

VSET2 is an input to voltage reference/regulator circuit 68. It is coupled to $V_{DD}$ through a resistor (Pad 16). It is also used to trim VREF.

XMIT is generated by communication modem circuit 60. It enables the transmitter output.

XTAL1 is an external connection to one terminal of a 76.8 kHz oscillator/resistor circuit (Pad 6). It is an input to crystal oscillator circuit 48.

XTAL2 is an external connection to one terminal of a 76.8 kHz oscillator/resistor pair (Pad 7). It is an input to crystal oscillator circuit 48.

XTRM is an external connection to $V_{DD}$ through a resistor (Pad 5). It sets the bias current on, for example, the 76.8 kHz crystal oscillator.

ZEROCLK is generated by PPM decoder circuit 58. It is the decoded clock signal corresponding to a logic level zero in the communications protocol.

FIGS. 5a and 5b depict left and right halves of a block diagram of integrated circuit 46 that may be used in the embodiments depicted in FIGS. 1–2b. In this embodiment, integrated circuit 46 has 28 external connections, pads 1 through 28. Internally, integrated circuit 46 includes a crystal oscillator circuit 48, a power on reset circuit 50, a main time base circuit 52, an output driver circuit 54, a transmitter circuit 56, a PPM decoder circuit 58, a communication modem circuit 60, a electrode status circuit 62, a receiver circuit 64, a battery status circuit 66, and a voltage reference/regulator circuit 68.

Crystal oscillator circuit 48 generates a regular 76.8 kHz clock signal labeled C76_8. This circuit has three external connections, XTRM, XTAL1, and XTAL2, and one input GND_REF. Power on reset circuit 50 generates three reset outputs, NRESET, NRSTPRG, NRST, to put all other circuits in an initial condition after powering up. This circuit has four inputs, C76_8, C1_49, NSTRT and IPOR, and two test points, TEST and TP6.

Main time base circuit 52 generates the pulse timing signals for control of the output driver circuit 54, and provides a 24-hour timer for integrated circuit 46. This circuit generates 8 outputs, BIASON, NIPLUS, IMINUS, IMINUS2, NOUT_ON, NEN_ANL, ANL_CLK, and C1_49. This circuit has six inputs, NRESET, REC_OFF, C76_8, DCON, STIM0, STIM1, and two test points, TEST and TP1.

Output driver circuit 54 controls the output signal, OUT1 and OUT2 delivered to the patient through pins 130. This circuit has inputs GND_REF, NOUT_ON, IMINUS, IMINUS2, NIPLUS, and BIASON and external connections ILIMIT, ITRM, and SYMTRM.

Transmitter circuit 56 combines the pulse timing parameters from PPM decoder 58 with the data output from communication modem 60 to transmit a low frequency magnetic pulse to an external receiver through NTRANS_OUT. This circuit has inputs C76_8, STARTCLK, ONECLK, ZEROCLK, TCODE and XMIT.

PPM decoder circuit 58 determines if received information from receiver circuit 64 is a valid down-link communication. Also, PPM decoder circuit 58 generates the pulse position protocol used by transmitter circuit 56. This circuit has outputs C38_4, NPPMRST, DSTB, DATA, STARTCLK, REC_OFF, ZEROCLK, ONECLK. PPM decoder circuit 58 also has inputs C76_8, NREC_OUT, NTRANS, NRST, and 2 test points, TEST and TP4.

Communication modem circuit 60 controls the mode of operation of integrated circuit 46 through two of its output bits, STIM0 and STIM1. These two bits define possible modes of operation. For example, four modes of operation may be: off, four hours on/20 hours off, eight hours on/16 hours off, or continuously on. Also this circuit receives signals from battery status circuit 66 indicating the status of the battery (EOL and LOWBATT) and from electrode status circuit 62 indicating the impedance of the output pins or electrodes 130 (LDHIGH and LDLOW). The circuit then generates an 11-bit communication word and transmit enable (TCODE and XMIT) for transmission by transmitter circuit 56. Communication modem circuit 60 has eleven other inputs, NRSTPRG, C38_4, NPPMRST, DSTB, DATA, STARTCLK, REC_OFF, DCON, and CODE, two other outputs, NTRANS and NSTRT, and two test points, TEST and TP5.

Electrode status circuit 62 compares the impedance of the output pins or electrodes 130 with a predetermined threshold or thresholds. It has two outputs, LDLOW and LDHIGH. The circuit has inputs, NRST, IMINUS, ANL_CLK, DCON, NEN ANL, ILEAD, and connections to OUT1, OUT2, LDTRM1 gand LDTRM2, and two test points, TEST and TP2.

Receiver circuit 64 generates a digital output, NREC_OUT, from an analog input RECV. This signal is received from a device external to combined tissue/growth stimulator and external fixation device 120, such as the aforementioned external receiver. Receiver circuit 64 has an additional input IREC.

Battery status circuit 66 monitors the voltage supplied by the associated battery and signals the communication modem circuit 60 when the battery reaches two trip points with LOWBATT and EOL. This circuit has inputs, NRST, REC_OFF, C1_49, NEN_ANL, IBATT, and GND_REF, an external connection to EOLTRM and two test points, TEST and TP3. Voltage reference/regulator circuit 68 generates the bias currents used in integrated circuit 46: IPOR, IREC, IBATT, ILEAD, IDCON, ICODE, and ITEST. This circuit has inputs, VSET1, VSET2, and VREF and output GND_REF.

Figure 6:
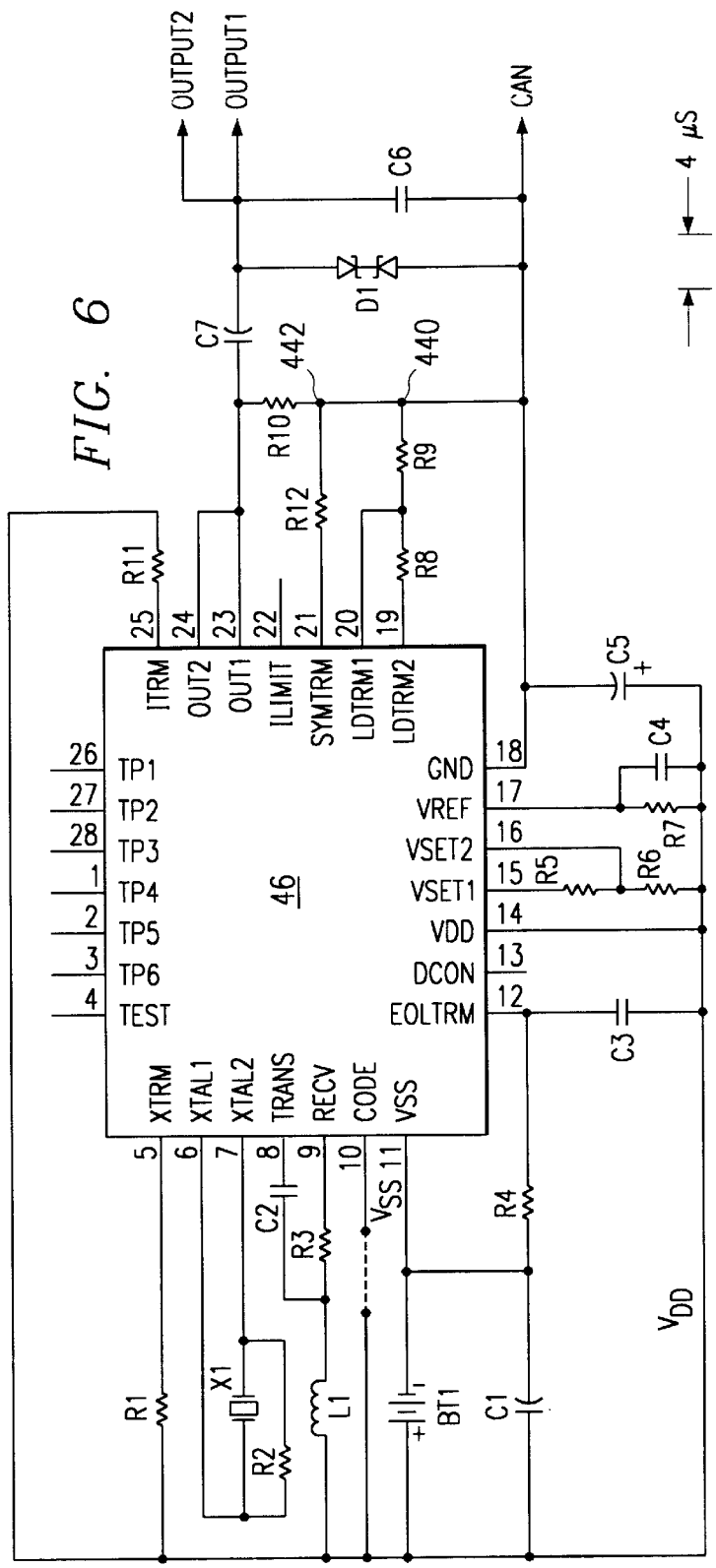
FIG. 6 illustrates schematically the circuit depicted in FIGS. 5a and 5b configured for an alternating current (AC) mode of operation.

FIG. 6 illustrates schematically the circuit depicted in FIGS. 5a and 5b configured for an AC mode of operation. When packaged, pins 1–4 and 26–28 may be left open on integrated circuit 46. Testing may be performed before final assembly.

XTRM is connected to $V_{DD}$ 5 through a resistor R1, and XTAL1 is connected to crystal X1 in parallel with resistor R2. XTAL2 is connected to the other terminal of crystal X1 and resistor R2. Crystal X1 is a 76.8 kHz crystal. TRANS, is connected to one terminal of capacitor C2. RECV is connected to the first terminal of external resistor R3. The remaining terminal of capacitor C2 and resistor R3 are tied together and to the first terminal of inductor L1. The second terminal of inductor L1 is connected to $V_{DD}$. CODE may or may not be connected to $V_{DD}$ through external pad 10. $V_{SS}$ is connected to the negative terminal of battery BT1, which may be a 2.8 volt lithium iodine battery rated for 200 mAH. A slightly larger battery may be substituted increasing the rating of the battery BT1 to 0.5 AH.

As depicted, $V_{SS}$ is also connected to one terminal of capacitor C1 and one terminal of resistor R4. The second terminal of capacitor C1 is connected to $V_{DD}$ and the second terminal of resistor R4 is connected to EOLTRIM. EOLTRIM is also connected to $V_{DD}$ through capacitor C3. Resistor R4 may be actively trimmed to achieve a desired LOWBATT trip point, such as 2.4 V, prior to final assembly. DCON is left floating at external pad 13. $V_{DD}$ is connected to the positive terminal of battery BT1. VSET1 is connected to $V_{DD}$ through resistor series combination of resistors R5 and R6. VSET2 is connected to the node formed by the inner connection of resistor R5 to resistor R6. VREF is connected to parallel resistor/capacitor combination. Parallel resistor capacitor combination includes resistor R7 and capacitor C4. The second terminal of R7 and C4 are connected to $V_{DD}$. Resistor R5 may be actively trimmed prior to assembly to generate GND=$V_{DD}$−1.5 Volts. GND is coupled to $V_{DD}$ through capacitor C5 and to an electrode window on the bone growth stimulator.

LDTRM2 is connected to a node 440 through a resistor series comprising resistors R8 and R9. Node 440 is connected to GND. LDTRM1 is connected to the node formed by the connection of resistors R8 and R9. The low lead impedance trip point is set by actively trimming resistor R9. The high impedance trip point is set by actively trimming resistor R8 after resistor R9. SYMTRIM is connected to a node 442 through optional resistor R12. SYMTRIM exits integrated circuit 46 at external pad 122. OUT1 is connected to the output electrode 30 through capacitor C7. Capacitor C7 ensures that the output has no net DC component. OUT1 is also connected to node 442 through resistor R10. Nodes 442 and 440 are electrically connected. OUT2 is connected to OUT1. ITRIM is connected to $V_{DD}$ through resistor R11. Resistor R11 is actively trimmed to set the output current. In addition, zener diode D1 is coupled between GND and output and are biased as depicted. They provide high voltage protection to the circuit. Capacitor C6 is also connected between OUTPUT1 and GND. Capacitor C6 protects the circuit from electromagnetic interference (EMI). The support elements are sized to provide galvanic current to the patient in accordance with the invention. For example, resistors R1–R12, capacitors C1–C6, and inductor L1 may all be sized to provide an output voltage level suitable to support the power requirements of combined external fixation device and tissue/bone growth stimulator 120.

Additional examples for circuitry that may be used in conjunction with the embodiments depicted in FIGS. 1–2b may be found in U.S. Pat. No. 5,565,005, filed Feb. 17, 1993 by John H. Erickson, et al., and entitled "Implantable Growth Tissue Stimulator and Method Operation", which is herein incorporated by reference.

Figure 7:
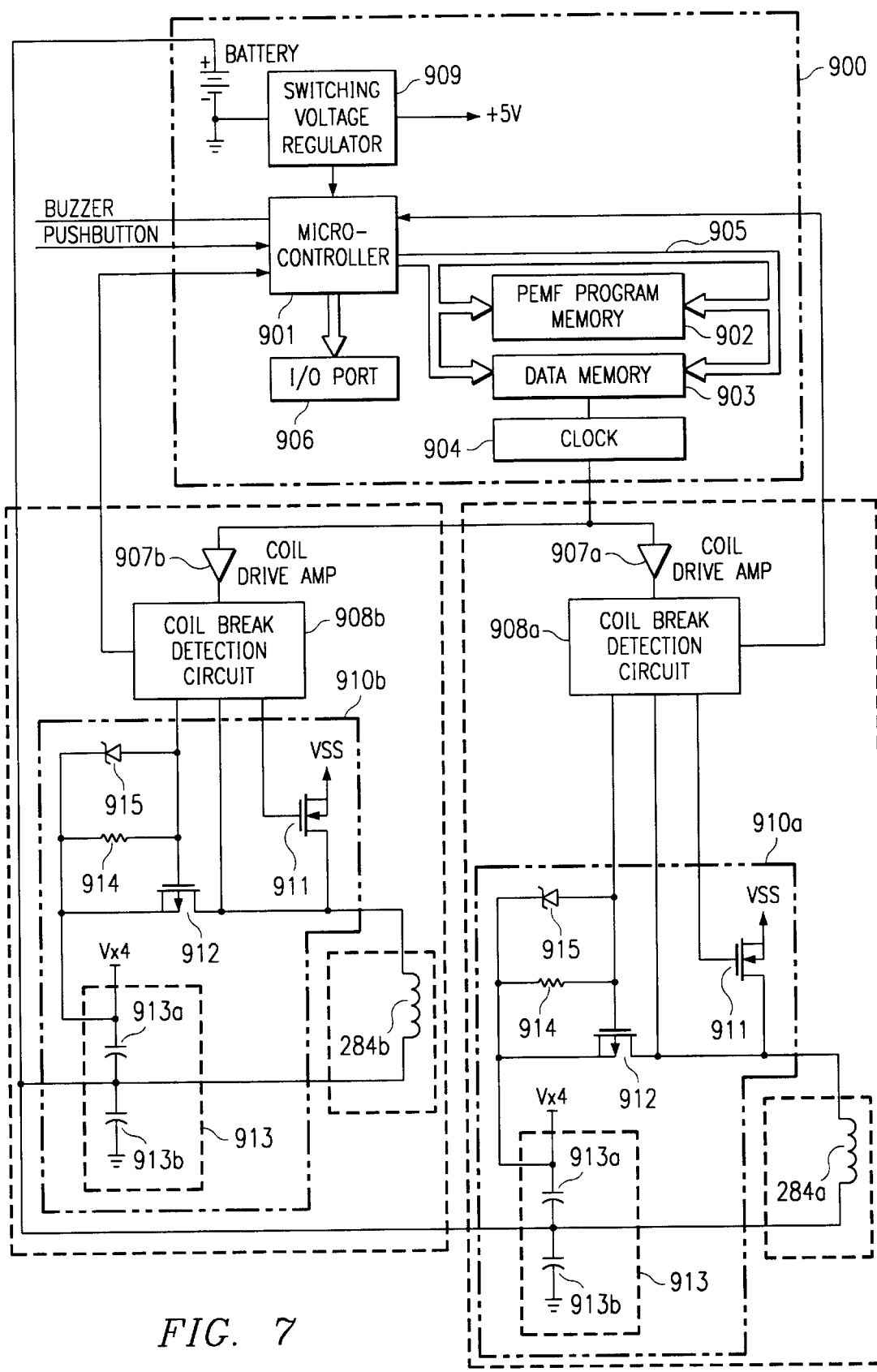
FIG. 7 is a schematic drawing of a block diagram of an electronic circuit and the transducer coils satisfactory for use with the combined tissue/bone growth stimulator and external fixation devices shown in FIGS. 3–4b.

FIG. 7 is a partly schematic and partly block diagram of one electrical circuit formed in accordance with teachings of the present invention. This electrical circuit may be used in conjunction with the embodiments depicted in FIGS. 3–4b. In the example of FIG. 7, this circuitry controls transducer coils 284a and 284b as discussed n conjunction with FIG. 1. This circuitry provides a pulsing bi-phasic current to transducer coils 284a and 284b at predetermined intervals, thereby activating the PEMF output signal according to a prescribed pre-programmed PEMF regimen. Except for transducer coils 284a and 284b, this circuitry may be physically located in control unit 150 or 350. The electrical circuitry includes both control circuitry 900, field sense circuitry 908 and drive circuitry 910, which all may be fabricated on a printed circuit board and encapsulated in control unit 150 or 350. In this embodiment, control circuitry 900 is operable to drive group circuitry 940a and 940b.

Control circuitry 900 includes processor or microcontroller 901, with associated integrated circuit components: a program memory 902, a data memory 903, and Real Time Clock circuit 904. For some applications, processor 901 may represent two individual microprocessors. One microprocessor may be used to control transducer coil 284a and the other microprocessor may be used to control transducer coil 284b.

Processor 901 is in data communication with these associated components by means of a bus 905. A PEMF program can be loaded into a microcontroller EPROM or other memory and installed as PEMF program memory 902. Alternatively, the PEMF program can be read into the PEMF program memory via I/O port 906.

Data memory 903 may be used to store data about the patient's use of combined tissue/bone growth stimulator and external fixation device 120, based on an internally maintained clock and calendar provided by clock circuit 904. For example, PEMF program parameters—such as start time, stop time, duration, and daily average—may be stored in data memory 903. This data can be read out or uploaded to any suitable printer, external device or communications link via the I/O port 906. In this embodiment, I/O port 906 is a recessed Serial Input/Output (SIO) port for connecting to such an external device.

Processor 901 controls coil drive amplifiers 907a and 907b, which drives the energization and de-energization of transducer coils 284a and 284b, respectively. Field sensor or coil break detection circuits 908a and 908b sense the electromagnetic fields output by respective transducer coils 284a and 284b and provide a response signal to processor 901 for monitoring the operation of combined tissue/bone growth stimulator and external fixation device 120. This built-in monitoring circuitry will ensure that the treatment field is being generated by proper current flow in each transducer coil 284b and 284a.

Processor 901 may store monitoring data in data memory 903, and will initiate a visible or audible warning signal or other alarm if the device is not generating the treatment field. If at any time during treatment either transducer 284b, 284a ceases to function properly, treatment will stop and the field fault indication is initiated.

In operation, processor 901 receives power from a power source, such as a nine-volt lithium or alkaline battery, through a switching voltage regulator 909. Regulator 909 provides +5 volts power to processor 901 and its associated digital components.

Processor 901 and its associated components may be implemented with conventional integrated circuit devices. For example, processor 901 may be a Motorola 68HC11 processor. The data memory 903 and clock circuit 904 may be a Dallas Semiconductor Corporation device.

The PEMF program may output a pair of control signals, each comprising a series of pulse bursts. The two signals have their pulses offset, such that a pulse of one signal is high when a pulse of the other signal is low. These alternating control signals control the drive electronics so that it switches current on and off at the proper times to provide bi-phasic current for transducer coils 284a and 284b.

A feature of the control signals is that at the beginning of one of the pulse bursts, its first pulse is shorter than the other pulses in the same pulse train. Thus, for example, if the first pulse train has pulses with 4 microseconds (4 $\mu$sec) on and 12 microseconds (12 $\mu$sec) off times, then the first pulse of the first pulse train is 2 microseconds (2 $\mu$sec). This first short pulse sets up the magnetic field for the PEMF stimulation therapy signal in the single-winding coil. By turning on the drive circuitry for one-half pulse, energization of the magnetic field takes place to set the PEMF magnetic field away from zero. Then, the next pulse on the other pulse train turns on for approximately twelve microseconds. This sets the current so that the drive flyback energy goes in a negative direction. This causes current to flow from an initial negative direction. The current then ramps up through zero and increases from a negative number through zero to a positive number during the pulse.

Drive electronics 910a and 910b drive respective transducer coils 284a and 284b, so that transducer coils 284a and 284b then generate the desired PEMF stimulation therapy signals. Drive electronics 910a and 910b have a first transistor switch 911 between break detection circuit 908 and transducer coils 284a and 284b, and a second transistor switch 912 between energy recovery capacitance circuit 913 and transducer coils 284a and 284b. Switches 911 and 912 control the output signal from transducer coils 284a and 284b. In operation, each transducer coil 284a and 284b shapes the pulsed electromagnetic field pattern and recovers unused energy during the interpulse collapse of the generated field.

For initialization, each switch 911 is turned on by respective coil drive amplifier 907a and 907b to present battery voltage across transducer coils 284a and 284b for a period of one-half a normal pulse duration of typically four microseconds (4 μsec). Activation current flows through transducer coils 284a and 284b to generate an output signal. When switch 911 switches off, switch 912 switches on to charge energy recovery capacitance circuit 913 to a voltage equal to four times the battery voltage. This causes transducer coils 284a and 284b to discharge in the opposite direction during the off period of switch 911 as compared to the direction during its on period. Thus, energy recovery occurs without a secondary coil. Drive circuits 910a and 910b permit sequencing of the current through respective transducer coils 284a and 284b in both directions.

Therefore, for a given magnetic field strength, the peak current can be cut in half. This results in a factor of four reduction in $I^2R$ losses, where I is the instantaneous coil current and R is the resistance of the coil winding. These are the types of losses that would exist with the use of a secondary winding. The voltage $V_{X4}$ may be derived using the flyback pulse from transducer coils 284a and 284b, instead of requiring a separate voltage boost circuit. By balancing the capacity of capacitors 913a and 913b, it is possible to eliminate the need for a separate four-times voltage supply circuit.

In the example of FIG. 4, energy recovery capacitance circuit 913 includes two series connected capacitors 913a and 913b. Their capacitance ratio is at least 1:3, and in the example of this description is 1:10 (in microfarads). Various other capacitor configurations could be used for capacitance circuit 913, with the common characteristic that it provides the desired energy restoring voltage, here $V_{X4}$. For example, energy recovery capacitance circuit 913 could include a capacitor and voltage regulator circuitry.

Control circuitry 900 is also operable to drive a single group circuitry or additional group circuitry(not explicitly shown). For example, control circuitry 900 may control single group circuitry where combined tissue/bone growth stimulator and external fixation device 120 utilizes a single coil 284a by removing group circuitry 907b. In such an embodiment, control circuitry 900 may control single group circuitry such as a single coil 384 as is illustrated in FIGS. 2a and 2b, without substantively altering the load on control circuitry 900. Alternatively, additional group circuitry may be placed further in parallel with group circuitry 940a and 940b without substantively altering the load on control circuitry 900. Thus, any number of group circuitry modules may be releasably coupled to control circuitry 900, and operated in conjunction with transducer coils 284a and 284b.

Figure 8A:
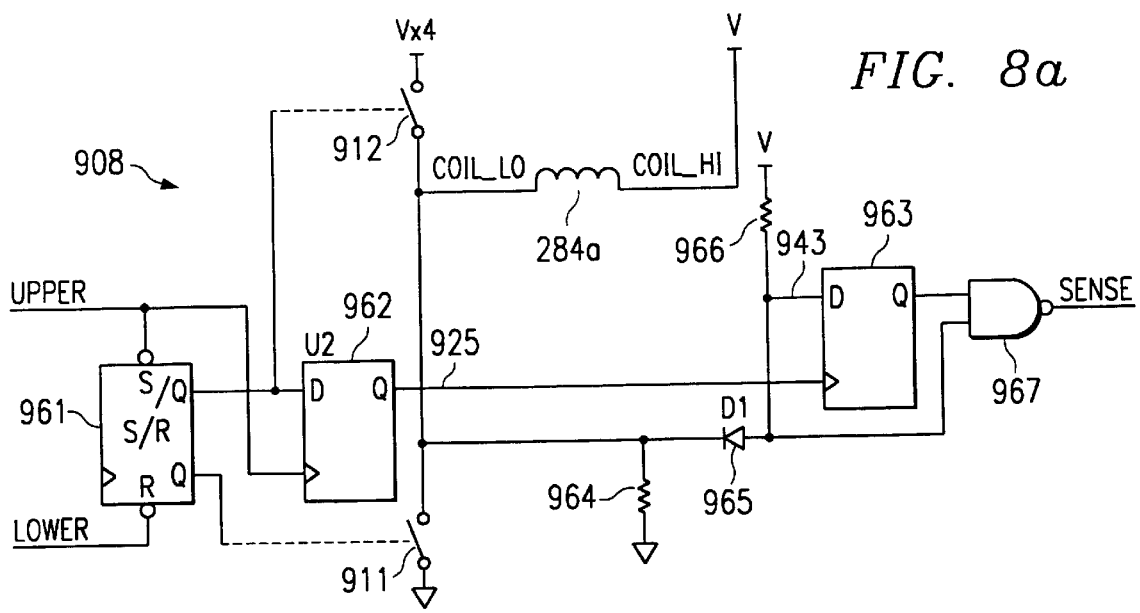
FIG. 8a is a schematic drawing showing the coil break detector circuit of FIG. 7.

FIG. 8a illustrates one embodiment of coil break detection circuit 908a. A set/reset flip-flop 961 receives an upper input signal and a lower input signal. One of its Q outputs goes to flip-flop 962 and controls the operation of switch 912. The other Q output controls the operation of switch 911. The Q output from flip-flop 962 goes to flip-flop 963 as a clock signal. Switch 912 controls whether the COIL_LO signal goes to $V_{X4}$, while switch 911 shunts COIL_LO to ground. The COIL_HI signal provides supply voltage V.

Resistor 964 and diode 965 receive supply voltage, V, from resistor 966. Flip-flop 963 receives as its D input the output from resister 966. The Q output from flip-flop 963 goes to NAND gate 967 to generate a sense output.

Figure 9B:
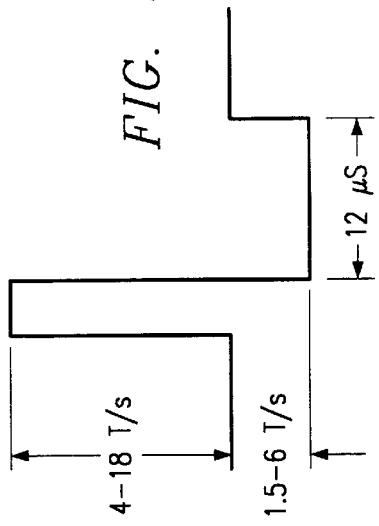
FIGS. 9a and 9b illustrate typical examples of output waveforms that may be associated with a combined tissue/bone growth stimulator and external fixation device.
Figure 9A:
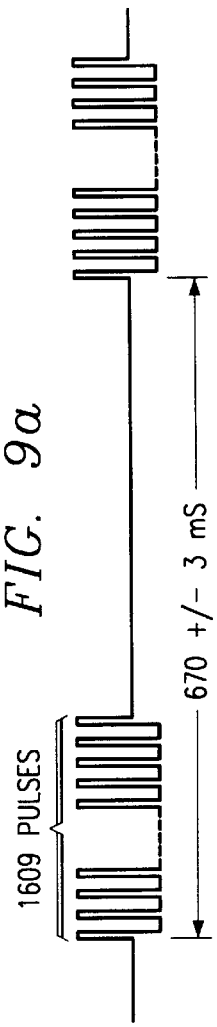

The voltage $V_{X4}$ is four times the voltage V, both being measured with respect to ground. The UPPER and LOWER signals consist of a burst of pulses, separated by an inter-burst period, as shown in FIGS. 9a and 9b. These two signals are essentially non-overlapping ensuring the stable operation of the S/R flip-flop 961. The Q outputs of S/R flip-flop 961 are of opposite state and are also essentially non-overlapping, ensuring that switches 911 and 912 are never simultaneously on.

During the inter-burst period, both switches 911 and 912 are open. Under normal operating conditions, transducer coil 284a will pull the COIL_LO signal level to the supply voltage V. If a break should occur in the coil, the COIL_LO signal will be pulled to ground by resistor 964.

Resistor 966, resistor 964, and diode 965 translate the COIL_LO signal to levels appropriate for the inputs of flip-flop 963 and NAND gate 967. The ratio of resistor 966 to resistor 964 is selected to provide a logic level "0" at the inputs of flip-flip 963 and NAND gate 967 should a break occur in transducer coils 284a and 284b.

The output of flip-flop 962 is a single pulse occurring at the beginning of a burst, beginning with the first pulse of UPPER and terminating on the second pulse of UPPER. The rising edge of the output of flip-flop 962 occurs prior to the first rising edge of COIL_LO due to the relatively short time delay associated with flip-flop 962 versus switch 912 and switch 911. The pulse output of flip-flop 962 goes to flip-flop 963, samples the inter-burst voltage. If the inter-burst voltage is equal to V, the Q output of flip-flop 963 is a logic level "1" until the next sampling pulse, thereby enabling output of the inverse of the COIL_LO signal to processor 901 as the SENSE signal.

If the inter-burst voltage is at a ground level, due to a break in the transducer coil 284a, the output of flip-flop 963 is set to a logic level "0", disabling the output of the inverse of the COIL_LO signal to processor 901.

A short across the coil terminals will cause the COIL_LO signal to be tied to V. The output of flip-flop 963 will be a logic level "1," therefore the output of NAND gate 967 will be a logical level "0" rather than the burst signal that processor 901 normally expects. This indicates the existence of a field fault condition. Connecting either the COIL_HI or COIL_LO terminal to ground, will essentially create a DC short.

Figure 8B:
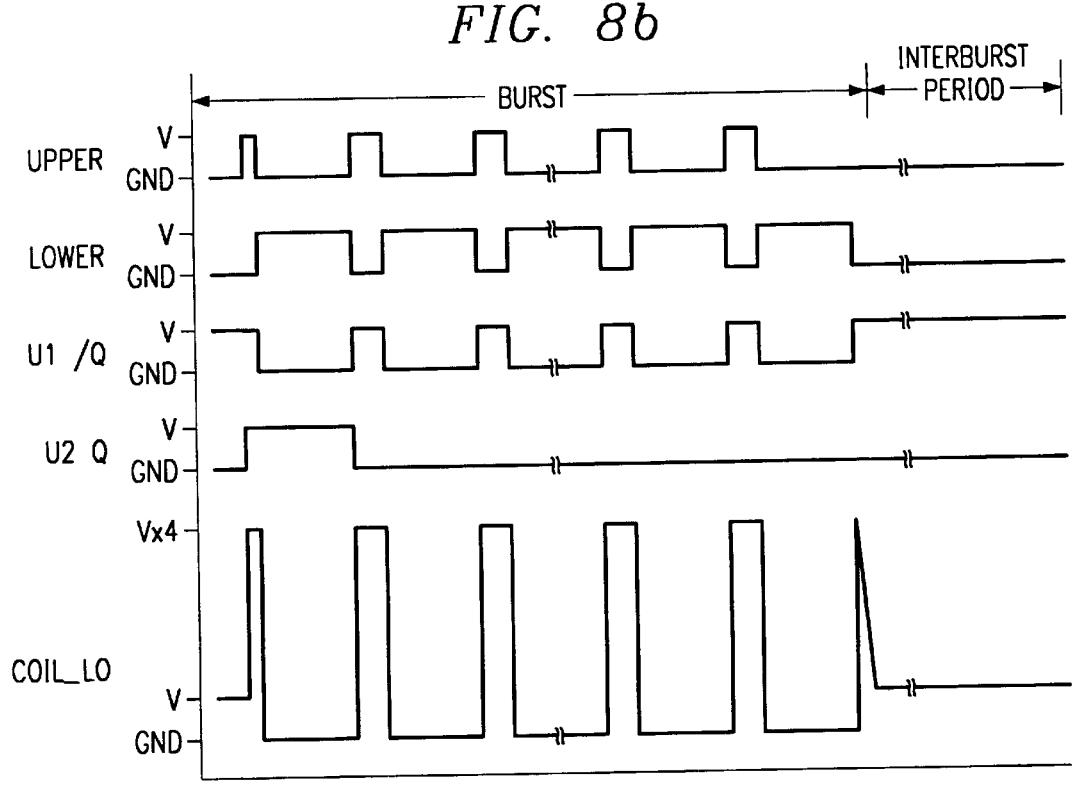
FIG. 8b is a drawing which illustrates the input logic versus signal provided to the transducer drive circuit shown in FIG. 7.

FIG. 8b illustrates the timing relationship of the logic signals that drive switches 911 and 912, as well as signals internal to coil break detection circuit 908. In each logic burst signal, there are a number of pulses, the duration of each upper pulse being only one-third the duration of lower pulse. Other parameters may also be used.

FIGS. 9a and 9b illustrate typical examples of output waveforms that may be associated with a combined tissue/bone growth stimulator and external fixation device. Utilization of waveforms such as these may provide, for example, an increase in bone density, because bone tissue appears to be responsive to various harmonic content within an electrical signal.

In some applications, the PEMF signal generated by a tissue/bone growth stimulator and external fixation device 120 or 220 in response to signals from control units 150 or 250, respectively, may include a burst of pulses that may be followed by an inter-burst period. FIG. 9a illustrates one example of a burst of pulses. For example, it may be particularly advantageous to produce a burst of one thousand six hundred nine (1609) pulses, at a repetition rate of approximately one and one-half pulse bursts per second. This rate corresponds to one burst approximately every 667+/−3 milliseconds (msec).

In each logic burst signal, there may be a number of pulses, where an individual pulse consists of a positive (energization) portion and a negative (de-energization) portion. As shown in FIG. 9b, a positive pulse width may be approximately four microseconds (4 $\mu$sec). The negative pulse width may be approximately twelve microseconds (12 $\mu$sec). This pulse period is approximately sixteen microseconds (16 $\mu$sec) for a pulse frequency of approximately 62.5 kilohertz. For the example of FIGS. 9a and 9b, there may be 1609 pulses per burst. The pulse widths for each portion may vary, depending on the application. For example, in other applications, it may be desirable for a positive pulse width to be approximately sixty-five microseconds (65 $\mu$sec) and the negative pulse width to be approximately one hundred ninety-five microseconds (195 $\mu$sec), for a pulse period of approximately two hundred sixty microseconds (260 $\mu$sec).

The areas of these portions may be approximately equivalent. For example, the duration of a positive portion is approximately one-third the duration of a negative portion, while the amplitude of the positive portion is about three times that of the negative portion. Other parameters may also be used. In some applications, it may be desirable to include a minimum and/or maximum amplitude threshold for each pulse portion.

Such a combination of parameters may be particularly advantageous. For example, these parameters may increase energy efficiency where transducer coils 284a, 284b may be large. These parameters may also reduce the operating requirements for battery power. The invention may also use other timing parameters to achieve the desired PEMF signals.

Although the present invention and its advantages have been described in detail, it should be understood that various changes, substitutions, and alterations can be made therein without departing from the spirit and scope of the invention as defined by the following claims.

What is claimed is:

1. Apparatus for treatment of fractures, osteotomies, soft tissue injuries, and reconstructive surgery using an electromagnetic field, comprising:

an external fixation device for stabilization of a selected portion of a patient, wherein the external fixation device includes at least two insulated stabilizing devices operable to direct a current from the external fixation device to a respective patient interface associated with each of the stabilizing devices;

the at least two stabilizing devices coated with an electrically non-conductive material;

a tissue/bone growth stimulator having a housing attached to and forming an integral component of the external fixation device;

a respective insulating coupler conducting the current between the housing and one of the stabilizing devices; and the tissue/bone growth stimulator operable to provide the electromagnetic field by directing the current between the housing and at least one inductive transducer provided on one of the at least two insulated stabilizing devices to stimulate growth of bone and tissue.

2. The apparatus of claim 1, wherein the current is an alternating current.

3. The apparatus of claim 1, wherein the tissue/bone growth stimulator is further operable to treat multiple areas of the patient simultaneously.

4. The apparatus of claim 1, wherein the tissue/bone growth stimulator is further operable to treat multiple bones and joints of the same patient.

5. The apparatus of claim 1, wherein the size and angulation of the external fixation device is selectively adjustable.

6. The apparatus of claim 1, wherein the electromagnetic field comprises a plurality of pulses with a pulse width of approximately ten microseconds to two hundred sixty microseconds.

7. The apparatus of claim 1, wherein the electromagnetic field comprises a plurality of pulses each having one of the group consisting of a predetermined minimum amplitude and a predetermined maximum amplitude.

8. The apparatus of claim 1, further comprising the tissue/bone growth stimulator operable to prevent infection by directing the electromagnetic field toward patient-hardware interfaces.

9. The apparatus of claim 1, wherein the selected portion comprises a joint rather than a single bone.

10. The apparatus of claim 1, wherein the external fixation device comprises a window through which the selected portion of the patient may be monitored.

11. The apparatus of claim 1, wherein the external fixation device comprises radiolucent material through which the selected portion of the patient may be radiographically imaged.

12. A method for treatment of fractures, osteotomies, soft tissue injuries and reconstructive surgery using an electromagnetic field, comprising:

applying an external fixation device to a selected portion of a patient's body using at least two insulated stabilizing devices to provide desired stability and maintain alignment of adjacent bone portions during a healing process;

stimulating the patient with a pulsed current conducted between a control unit attached to external fixation device and at least one inductive transducer provided on one of the at least two insulated stabilizing devices to create the electromagnetic field; and penetrating with the electromagnetic field directly into a targeted area between the at least two insulated stabilizing devices.

13. The method of claim 12, further comprising monitoring the time the patient has received the pulsed current stimulation.

14. The method of claim 12, further comprising stimulating tissue growth of the patient within the selected portion.

15. The method of claim 12, further comprising stimulating bone growth of the patient within the selected portion.

16. The method of claim 12, further comprising reducing a risk of infection at an interface between the patient and the external fixation device by creating the electromagnetic field.

17. The method of claim 12, further comprising pulsing current through the two stabilizing devices to create a radial-directed treatment volume of the electromagnetic field directed at a patient interface.

18. The method of claim 12, further comprising stimulating the patient within a treatment volume including the patient's knee.

19. The method of claim 12, further comprising stimulating the patient with a plurality of pulses with a pulse width of approximately ten microseconds to two hundred sixty microseconds.

20. The method of claim 12, further comprising stimulating the patient with a plurality of pulses each having one of the group consisting of a predetermined minimum amplitude and a predetermined maximum amplitude.

21. The method of claim 12, further comprising monitoring the selected portion of the patient's body through a window of the external fixation device.

22. The method of claim 21, further comprising using at least one of radiographic imaging, ultrasonic imaging, and visual examination for the monitoring.

23. The method of claim 12, further comprising monitoring the injured portion of the patient's body through a radiolucent portion of the external fixation device.

24. A method for the treatment of fractures, osteotomies, soft tissue injuries and reconstructive surgery using an electromagnetic field, comprising:
applying an external fixation device with at least two pins to a selected portion of a patient's body to provide stability during a healing process;
conducting a current between a control unit attached to the external fixation device and a plurality of transducer coils respectively disposed adjacent to the at least two pins;
pulsing the current to create the electromagnetic field from the plurality of transducer coils of the tissue/bone growth stimulator; and
penetrating directly into a targeted area adjacent to the at least two pins using the electromagnetic field.

25. The method of claim 24, further comprising producing the electromagnetic field with an alternating current.

26. Apparatus for treatment of fractures, osteotomies, soft tissue injuries, and reconstructive surgery using an electromagnetic field, comprising:
an external fixation device for stabilizing a selected portion of a patient;
the external fixation device having at least two stabilizing pins;
a tissue/bone growth stimulator having a control unit attached to and forming an integral component of the external fixation device;
at least two insulating couplers attached to and extending from the control unit to conduct current from the control unit to at least one transducer coil;
the at least one transducer coil disposed on the external fixation device adjacent an interface between the stabilizing pins and the patient; and
the tissue/bone growth stimulator operable to generate the electromagnetic field at the at least one transducer coil.

27. The apparatus of claim 26, wherein the tissue/bone growth stimulator comprises a plurality of transducer coils operable to generate respective electromagnetic fields.

* * * * *